(12) United States Patent
Lemaire et al.

(10) Patent No.: US 7,183,279 B2
(45) Date of Patent: Feb. 27, 2007

(54) HISTOGRANIN-LIKE PEPTIDES AND NON-PEPTIDES, PROCESSES FOR THEIR PREPARATION AND USES THEREOF

(75) Inventors: Simon Lemaire, Aylmer (CA); Irma Bernatchez-Lemaire, Aylmer (CA); Hoang-Thanh Le, Ottawa (CA)

(73) Assignee: University of Ottawa, Ottawa (CA)

( * ) Notice: Subject to any disclaimer, the term of this patent is extended or adjusted under 35 U.S.C. 154(b) by 0 days.

(21) Appl. No.: 11/440,727

(22) Filed: May 25, 2006

(65) Prior Publication Data

US 2006/0252673 A1   Nov. 9, 2006

(51) Int. Cl.
```
A61K 31/535    (2006.01)
A61K 31/445    (2006.01)
A61K 31/415    (2006.01)
C07D 235/04    (2006.01)
C07D 235/06    (2006.01)
C07D 235/08    (2006.01)
C07D 403/02    (2006.01)
C07D 211/26    (2006.01)
C07D 211/32    (2006.01)
C07D 295/00    (2006.01)
C07D 295/12    (2006.01)
C07D 233/61    (2006.01)
C07D 265/30    (2006.01)
```
(52) U.S. Cl. .................. 514/235.5; 514/237.5; 514/317; 514/322; 514/394; 548/304.4; 548/305.4; 548/335.5; 564/152; 544/139; 544/159; 546/199; 546/229

(58) Field of Classification Search ............ None
See application file for complete search history.

(56) References Cited

U.S. PATENT DOCUMENTS 5,169,833 A    12/1992    Hansen, Jr. et al.

FOREIGN PATENT DOCUMENTS

CA           2219437           4/1999

(Continued)

OTHER PUBLICATIONS

Lemaire et al.; Isolation and characterization of histogranin, a natural peptide with NMDA receptor antagonist activity, *European Journal of Pharmacology-Molecular Pharmacology Section*, vol. 245, 1993, pp. 247-256.

(Continued)

*Primary Examiner*—Cecilia J. Tsang
*Assistant Examiner*—Andrew D. Kosar
(74) *Attorney, Agent, or Firm*—Welsh & Katz, Ltd.

(57) ABSTRACT

The invention relates to new basic amino acid derivatives of general formulae I, II and III, and the preparation and use thereof in treatment of pain. The compounds have histogranin-like antinociceptive, morphine potentiating and COX-2 induction modulating activities.

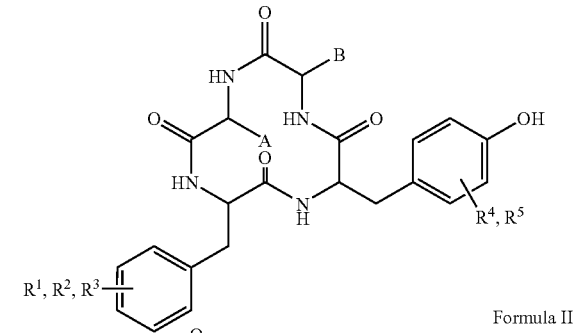

Formula I

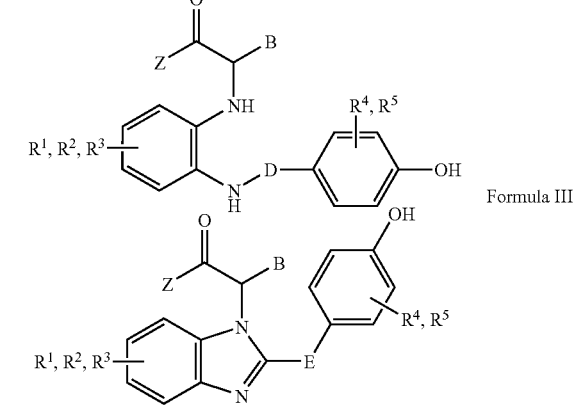

Formula II

Formula III wherein:

A is -hydrogen, —$(C_1$–$C_8)$alkyl or —$(C_1$–$C_8)$alkyl substituted by hydroxy;

B is —$(C_1$–$C_6)$alkylguanidino, —$(C_1$–$C_6)$alkyl(4-imidazolyl), —$(C_1$–$C_6)$alkylamino, p-aminophenylalkyl $(C_1$–$C_6)$—, p-guanidinophenylalkyl$(C_1$–$C_6)$— or 4-pyridinylalkyl$(C_1$–$C_6)$—;

D is —(CO)—, —(CO)—$(C_1$–$C_6)$alkylene or —$(C_1$–$C_6)$alkylene;

E is a single bond or —$(C_1$–$C_6)$alkylene;

Z is —$NH_2$, —NH—$(C_1$–$C_6)$alkylcarboxamide, —NH—$(C_1$–$C_6)$alkyl, —NH— (N-benzyl), —NH-cyclo $(C_5$–$C_7)$ alkyl, —NH-2-(1-piperidyl)ethyl, —NH-2-(1-pyrrolidyl) ethyl, —NH-2-(1-pyridyl)ethyl, —NH-2-(morpholino) ethyl, -morpholino, -piperidyl, —OH, —$(C_1$–$C_6)$alkoxy, —O-benzyl or —O-halobenzyl;

$R^1$, $R^2$ and $R^3$ are, independent of one another, -hydrogen, -arylcarbonylamino, —$(C_1$–$C_6)$alkoylamino, —$(C_1$–$C_6)$ alkylamino, —$(C_1$–$C_6)$alkyloxy, —$(C_1$–$C_6)$alkylaminocarbonyl, -carboxy, —OH, -benzoyl, -p-halogenobenzoyl, -methyl, —S-(2,4-dinitrophenyl), —S-(3-nitro-2-pyridinesulfenyl), -sulfonyl, -trifluoromethyl, —$(C_1$–$C_6)$ alkylaminocarbonylamino, -halo or -amino;

$R^4$ and $R^5$ are, independent of one another, -hydrogen, —$(C_1$–$C_6)$alkyl, -methyloxy, -nitro, -amino, -arylcarbonylamino, —$(C_1$–$C_6)$alkoylamino, —$(C_1$–$C_6)$alkylamino, -halo or —OH.

8 Claims, 6 Drawing Sheets

FOREIGN PATENT DOCUMENTS

EP        0419210        3/1991

OTHER PUBLICATIONS

Boarder et al.; "Met-Enkephalin [Arg[6], Phe[7]] Immunoreactivity in Bovine Caudate and Bovine Adrenal Medulla," *Journal of Neurochemistry*, vol. 39 (1), 1982, pp. 149-154.

Liston et al.; "Processing of Proenkephalin is Tissue-Specific," *Science*, vol. 225, Aug. 17, 1984, pp. 734-737.

Lemaire et al.; "Central and Peripheral Non-Opioid Analgesic Activity of Histogranin and Related Peptides," *Society of Neuroscience*, vol. 23, 1997, Paragraph No. 267.13, 1 page.

Ruan et al.; "Non-poioid antinociceptive effects of supraspinal histogranin and related peptides: Possible involvement of central dopamine $D_2$ receptor," *Pharmacology Biochemistry and Behavior*, vol. 67, 2000, pp. 83-91.

Shukla et al.; "*N*-Methyl-D-Aspartate Receptor Antagonist Activity and Phencyclidine-Like Behavoiral Effects of the Pentadecapeptide, [Ser[1]Historanin," *Pharmacology Biochemistry and Behavior*, vol. 50 (1), 1995, pp. 49-54.

Siegan et al.; "A natural peptide with NMDA inhibitory activity reduces tonic pain in the formalin model," *Neuroreport*, vol. 8 (6) Apr. 14, 1997, pp. 1379-1381.

Siegan et al.; "Suppression of neuropathic pain by a naturally-derived peptide with NMDA antagonist activity," *Brain Research*, vol. 755, 1997, pp. 331-334.

Hama et al.; "NMDA-Induced Spinal Hypersensitivity Is Reduced by Naturally Derived Peptide Analog [Ser[1]]Histogranin," *Pharmacology Biochemistry and Behavior*, vol. 61 (1), 1999, pp. 67-74.

Rogers et al.; "Characterization of [$^{125}$I][Ser[1]]Histogranin Binding Sites in Rat Brain[1]," *The Journal of Pharmacology and Experimental Therapeutics*, vol. 267(1), 1993, pp. 350-356.

Lemaire et al.; "Characterization of Histogranin Receptors in Human Peripheral Blood Lymphocites," *Biochemical and Biophysical Research Communications*, vol. 194(3), pp. 1323-1329.

Nishino, et al.; "cyclo(-arginyl-sarcosyl-aspartyl-phenylglycyl$_{-2}$ Simple synthesis of an RGD-related peptide with inhibitory activity for platelet aggregation," *J. chem. . Socl, Perkin Trans. 1*, 1996, pp. 939-946.

Osapay et al.; "Synthesis of Tyrocidine A: Use of Oxime Resin for Peptide Chain Assembly and Cyclization," *Tetrahedron Letters*, vol. 31 (43), 1990, pp. 6121-6124.

Kaiser et al.; "Color Test for Detection of Free Terminal Amino Groups in the Solid-Phase Synthesis of Peptides,"*Anal. Biochem.*, vol. 34, 1970, pp. 595-598.

Matsueda et al.; "A *p*-Methylbenzhydrylamine Resin for Improved Solid-Phase Synthesis of Peptide Amides[1]," *Peptides*, vol. 2, 1981, pp. 45-50.

Lee et al.; "Solid Phase Synthesis of 3.4-Disubstituted-7-carbamoyl-1,2,3,4-tetrahydroquinoxalin-2-ones," *J. Org. Chem.*, vol. 62, 1997, pp. 3874-3879.

Backes et al.; "Activation Method to Prepare a Highly Reacitve Acylsulfonamide 'Safety-Catch' Linker for Solid-Phase Synthesis," *J. Am. Chem. Soc.*, vol. 118, 1996, pp. 3055-3-56.

Lemaire et al.; "Synthesis and biological activity of dynorphin-(1-13) and analogs substituted in positions 8 and 10," *Int. J. Peptide Protein Res.*, vol. 27, 1986, pp. 300-305.

D'Amour et al.; "A Method for Determining Loss of Pains Sensation," *The Biologic Research Laboratory, University of Denver*, Jan. 27, 1941, pp. 74-79.

Abstract; "role of D1/D2 dopamine and N-methyl-D-aspartate (NMDA) receptors in morphine tolerance and dependence in mice," *Euro. Neuropsychopharmacol*, vol. 5(2), Jun. 1995, (pp. 81-87) 1 sheet.

Sufka et al.; "Stimulus properties and antinociceptive effects of selective bradykinin $B_1$, and $B_2$ receptor antagonists in rats," *Pain*, vol. 66, 1996, pp. 99-103.

Lemaire; "Characterization of the Bronchoalveolar Cellular Resposne in Experimental Asbestosis," *Am. Rev. Respir. Dis. 1985*, vol. 131, pp. 144-149.

Hayashi et al.; "The Type of Analgesic-receptor Interaction Involved in Certain Analgesic Assays," *European Journal of Pharmacology*, vol. 16, 1971, pp. 63-66.

SEQUENCE LISTING

```
<160> NUMBER OF SEQ ID NOS: 9

<210> SEQ ID NO 1
<211> LENGTH: 15
<212> TYPE: PRT
<213> ORGANISM: Artificial
<220> FEATURE:
<223> OTHER INFORMATION: Prior art peptide synthesized by solid-phase
      procedure

<400> SEQUENCE: 1

Met Asn Tyr Ala Leu Lys Gly Gln Gly Arg Thr Leu Tyr Gly Phe
1               5                   10                  15

<210> SEQ ID NO 2
<211> LENGTH: 15
<212> TYPE: PRT
<213> ORGANISM: Artificial
<220> FEATURE:
<223> OTHER INFORMATION: Prior art peptide synthesized by solid-phase
```

```
                              procedure

<400> SEQUENCE: 2

Val Val Tyr Ala Leu Lys Arg Gln Gly Arg Thr Leu Tyr Gly Phe
1               5                   10                  15

<210> SEQ ID NO 3
<211> LENGTH: 14
<212> TYPE: PRT
<213> ORGANISM: Artificial
<220> FEATURE:
<223> OTHER INFORMATION: Prior art peptide synthesized by solid-phase
      procedure

<400> SEQUENCE: 3

Ala Leu Lys Arg Gln Gly Arg Thr Leu Tyr Gly Phe Gly Gly
1               5                   10

<210> SEQ ID NO 4
<211> LENGTH: 9
<212> TYPE: PRT
<213> ORGANISM: Artificial
<220> FEATURE:
<223> OTHER INFORMATION: Prior art peptide synthesized by solid-phase
      procedure

<400> SEQUENCE: 4

Gly Gln Gly Arg Thr Leu Tyr Gly Phe
1               5

<210> SEQ ID NO 5
<211> LENGTH: 4
<212> TYPE: PRT
<213> ORGANISM: Artificial
<220> FEATURE:
<223> OTHER INFORMATION: Cyclic tetrapeptide synthesized by solid-phase
      procedure
<220> FEATURE:
<221> NAME/KEY: Xaa
<222> LOCATION: (2)..(2)
<223> OTHER INFORMATION: Xaa is p-Cl-Phe
<220> FEATURE:
<221> NAME/KEY: Xaa
<222> LOCATION: (4)..(4)
<223> OTHER INFORMATION: Xaa is (D)-Arg

<400> SEQUENCE: 5

Gly Xaa Tyr Xaa
1

<210> SEQ ID NO 6
<211> LENGTH: 4
<212> TYPE: PRT
<213> ORGANISM: Artificial
<220> FEATURE:
<223> OTHER INFORMATION: Cyclic tetrapeptide synthesized by solid-phase
      procedure
<220> FEATURE:
<221> NAME/KEY: Xaa
<222> LOCATION: (2)..(2)
<223> OTHER INFORMATION: Xaa is p-Cl-Phe
<220> FEATURE:
<221> NAME/KEY: Xaa
<222> LOCATION: (4)..(4)
<223> OTHER INFORMATION: Xaa is p-amino-Phe

<400> SEQUENCE: 6

Gly Xaa Tyr Xaa
1
```

```
<210> SEQ ID NO 7
<211> LENGTH: 4
<212> TYPE: PRT
<213> ORGANISM: Artificial
<220> FEATURE:
<223> OTHER INFORMATION: Cyclic tetrapeptide synthesized by solid-phase
      procedure
<220> FEATURE:
<221> NAME/KEY: Xaa
<222> LOCATION: (2)..(2)
<223> OTHER INFORMATION: Xaa is p-Cl-Phe
<220> FEATURE:
<221> NAME/KEY: Xaa
<222> LOCATION: (4)..(4)
<223> OTHER INFORMATION: Xaa is p-guanidino-Phe

<400> SEQUENCE: 7

Gly Xaa Tyr Xaa
1

<210> SEQ ID NO 8
<211> LENGTH: 4
<212> TYPE: PRT
<213> ORGANISM: Artificial
<220> FEATURE:
<223> OTHER INFORMATION: Cyclic tetrapeptide synthesized by solid-phase
      procedure
<220> FEATURE:
<221> NAME/KEY: Xaa
<222> LOCATION: (2)..(2)
<223> OTHER INFORMATION: Xaa is p-amino-Phe
<220> FEATURE:
<221> NAME/KEY: Xaa
<222> LOCATION: (4)..(4)
<223> OTHER INFORMATION: Xaa is (D)-Arg

<400> SEQUENCE: 8

Gly Xaa Tyr Xaa
1

<210> SEQ ID NO 9
<211> LENGTH: 4
<212> TYPE: PRT
<213> ORGANISM: Artificial
<220> FEATURE:
<223> OTHER INFORMATION: Cyclic tetrapeptide synthesized by solid-phase
      procedure
<220> FEATURE:
<221> NAME/KEY: Xaa
<222> LOCATION: (2)..(2)
<223> OTHER INFORMATION: Xaa is p-Cl-Phe
<220> FEATURE:
<221> NAME/KEY: Xaa
<222> LOCATION: (4)..(4)
<223> OTHER INFORMATION: Xaa is (D)-Arg

<400> SEQUENCE: 9

Thr Xaa Tyr Xaa
1
```

HISTOGRANIN-LIKE PEPTIDES AND NON-PEPTIDES, PROCESSES FOR THEIR PREPARATION AND USES THEREOF

FIELD OF THE INVENTION

The present invention relates to pharmaceutical pounds for use in the management of pain. More particularly, it relates to histogranin-like peptides and non-peptides.

BACKGROUND OF THE INVENTION

Histogranin (HN, Scheme 1) (SEQ ID NO. 1), a pentadecapeptide whose structure presents 80% and 73% homologies with those of fragment-(86–100) of histone H4 (SEQ ID NO. 2) and osteogenic growth peptide (OGP) (SEQ ID NO. 3), respectively, was first isolated from extracts of bovine adrenal medulla (Lemaire, Eur. J. Pharmacol., 1993, 245, 247–256), a tissue recognized to contain various pain reducing substances, including the endogenous opioid peptides Met- and Leu-enkephalins and catecholamines (Boarder et al. J. Neurochem., 1982, 39, 149–154; Liston et al. Science, 1984, 225, 734–737).

I.c.v. administration of HN (SEQ ID NO. 1) and related peptides in mice dose-and structure-dependently blocked writhing induced by i.p. administration of acetic acid and tail-flick induced by radiant heat (Lemaire et al., Soc. Neurosci. 1997, 23, 674., Ruan, Prasad and Lemaire, Pharmcol. Biochem. Behav. 2000, 66, 1–9). In addition, [Ser¹]HN, a chemically stable analog of HN (SEQ ID NO. 1) (Shukla and Lemaire, Pharmcol. Biochem. Behav. 1995, 50, 49–54), blocked tonic pain in the rat formalin assay (Siegen and Sagan, Neuroreport. 1997, 8 1379–81) and attenuated hyperalgesia and allodynia caused by sciatic nerve injury (Siegan and Sagan, Brain Res. 1997, 755, 331–334) and intrathecal (i.t.) administration of N-methyl-D-aspartate (NMDA; Hama and Sagen, Pharmacol. Biochem. Behav., 1999, 62, 67–74).

Scheme 1:

Histogranin (HN) (SEQ ID NO. 1):

Met-Asn-Tyr-Ala-Leu-Lys-Gly-Gln-Gly-Arg-Thr-Leu-Tyr-Gly-Phe

H4-(86–100) (Histone H4 fragment) (SEQ ID NO. 2):

Val—Val-Tyr-Ala-Leu-Lys-Arg-Gln-Gly-Arg-Thr-Leu-Tyr-Gly-Phe

OGP (Osteogenic Growth Peptide) (SEQ ID NO. 3):
Ala-Leu-Lys-Arg-Gln-Gly-Arg-Thr-Leu-Tyr-Gly-Phe-Gly—Gly Histogranin(7–15) (SEQ ID NO. 4):

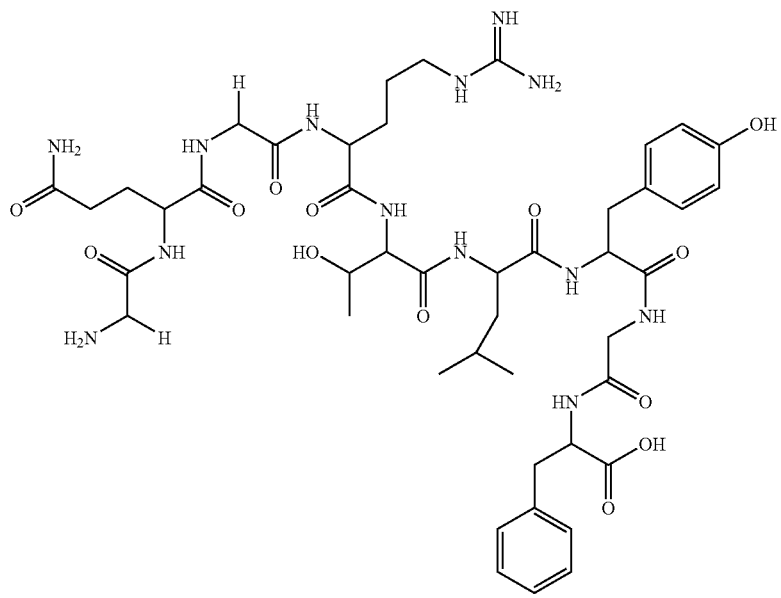

In the mouse writhing tail-flick assays, the analgesic effects of i.c.v. administration of HN (SEQ ID NO. 1) and related peptides are not mediated by opioid receptors and may involve a participation of dopamine D2 sites (Ruan, Prasad and Lemaire, Pharmcol. Biochem. Behav. 2000, 66, 1–9). A hypothesis is that HN (SEQ ID NO. 1) and related peptides bind to a specific receptor present in the brain (Roger et Lemaire, J. Pharmacol. Exp. Ther., 1993, 267, 350–356) and on peripheral cells (Lemaire et al., Biochem Biophys Res Commun. 1993, 194, 1323–9) and modulate processes involved in the pathophysiology of pain.

Among various HN related peptides and fragments, the C-terminal peptide HN-(7–15) (SEQ ID NO. 1) (Scheme 1) was shown to be particularly potent in the mouse writhing test with an $AD_{50}$ of 8.5 nmol/mouse as compared with 23 nmol/mouse for HN (SEQ ID NO. 1) (Ruan, Prasad and Lemaire, Pharmacol. Biochem. Behav. 2000, 66, 1–9; Canadian patent application 2,219,437).

SUMMARY OF THE INVENTION

There is provided a compound of general formula I, II or III, or a pharmaceutically acceptable salt thereof:

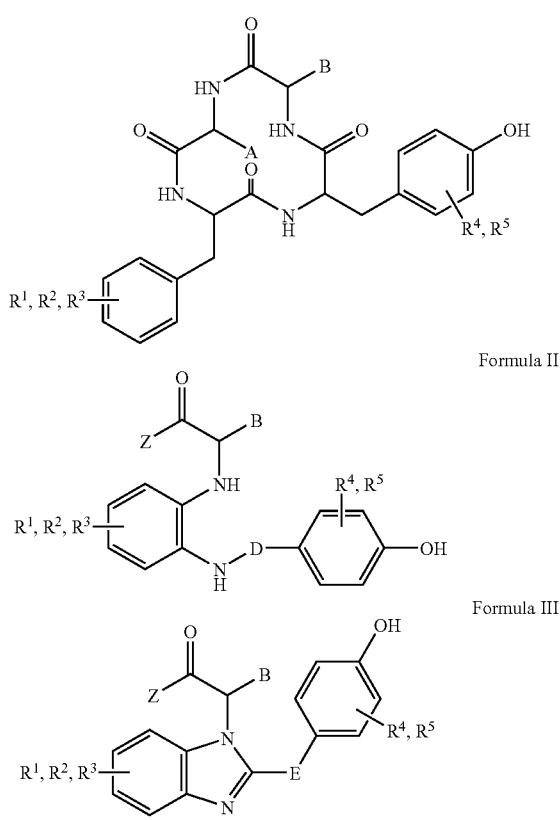

Formula I

Formula II

Formula III wherein:

A is -hydrogen, —(C$_1$–C$_8$)alkyl or —(C$_1$–C$_8$)alkyl substituted by hydroxy;

B is —(C$_1$–C$_6$)alkylguanidino, —(C$_1$–C$_6$)alkyl(4-imidazolyl), —(C$_1$–C$_6$)alkylamino, p-aminophenylalkyl (C$_1$–C$_6$)—, p-guanidinophenylalkyl(C$_1$–C$_6$)— or 4-pyridinylalkyl(C$_1$–C$_6$)—;

D is —(CO)—, —(CO)—(C$_1$–C$_6$)alkylene or —(C$_1$–C$_6$) alkylene;

E is a single bond or —(C$_1$–C$_6$)alkylene;

Z is —NH$_2$, —NH—(C$_1$–C$_6$)alkylcarboxamide, —NH—(C$_1$–C$_6$)alkyl, —NH-benzyl, —NH-cyclo(C$_5$–C$_7$)alkyl, —NH-2-(1-piperidyl)ethyl, —NH-2-(1-pyrrolidyl)ethyl, —NH-2-(1-pyridyl)ethyl, —NH-2-(morpholino)ethyl, -morpholino, -piperidyl, —OH, —(C$_1$–C$_6$)alkoxy, —O-benzyl or —O-halobenzyl;

R$^1$, R$^2$ and R$^3$ are, independent of one another, -hydrogen, -arylcarbonylamino, —(C$_1$–C$_6$)alkoylamino, —(C$_1$–C$_6$) alkylamino, —(C$_1$–C$_6$)alkyloxy, —(C$_1$–C$_6$)alkylaminocarbonyl, -carboxy, —OH, -benzoyl, -p-halogenobenzoyl, -methyl, —S-(2,4-dinitrophenyl), —S-(3-nitro-2-pyridinesulfenyl), -sulfonyl, -trifluoromethyl, —(C$_1$–C$_6$) alkylaminocarbonylamino, -halo or -amino;

R$^4$ and R$^5$ are, independent of one another, -hydrogen, —(C$_1$–C$_6$)alkyl, -methyloxy, -nitro, -amino, -arylcarbonylamino, —(C$_1$–C$_6$)alkoylamino, —(C$_1$–C$_6$)alkylamino, -halo or —OH.

There are also provided methods for synthesizing compounds of Formulae I, II and III.

There are also provided pharmaceutical compositions comprising a compound of Formulae I, II or III, or a pharmaceutically acceptable salt thereof, together with a pharmaceutically acceptable carrier, diluent or excipient.

In addition, there is provided a method for managing pain comprising administering a pain managing effective amount of a compound of Formulae I, II or III, or a pharmaceutically acceptable salt thereof, to a subject in need of pain management.

Furthermore, there is provided the use of a compound of Formulae I, II or III, or a pharmaceutically acceptable salt thereof, for managing pain or for manufacturing a medicament for managing pain.

There is also provided commercial packages comprising a compound of Formulae I, II or III, or a pharmaceutically acceptable salt thereof, or a composition comprising a compound of Formulae I, II or III, or a pharmaceutically acceptable salt thereof, together with instructions for their use for managing pain.

There is also provided a method of modulating COX-2 induction comprising administering an effective amount of a COX-2 induction modulating compound of Formulae I, II or III, or a pharmaceutically acceptable salt thereof, or a composition comprising a compound of Formulae I, II or III, or a pharmaceutically acceptable salt thereof, to a subject.

Compounds of Formulae I, II and III were invented according to the unifying hypothesis that compounds containing basic, hydroxyphenyl and phenyl groups (or homologues) with proper spatial arrangements display HN-like biological activities.

DETAILED DESCRIPTION OF THE INVENTION

The radical A is preferably hydrogen, CH$_3$CH(OH)— or (CH$_3$)$_2$CHCH$_2$—. The CH$_3$CH(OH)— or (CH$_3$)$_2$CHCH$_2$— groups may be bonded to the molecule in such a way as to provide either the R- or S-configuration at the carbon atom to which the group is bonded. As one skilled in the art will recognize, the hydrogen radical corresponds to the amino acid glycine, the group CH$_3$CH(OH)— has the same structure as the side-chain from the amino acid threonine while (CH$_3$)$_2$CHCH$_2$— has the same structure as the side-chain from the amino acid leucine.

The radical B is preferably H$_2$N—C(NH)—NH—CH$_2$CH$_2$CH$_2$— or H$_2$N—(CH$_2$)$_4$—. The H$_2$N—C(NH)—NH—CH$_2$CH$_2$CH$_2$— or H$_2$N—(CH$_2$)$_4$— groups may be bonded to the molecule in such a way as to provide either the R- or S-configuration at the carbon atom to which the group is bonded. As one skilled in the art will recognize, the group H$_2$N—C(NH)—NH—CH$_2$CH$_2$CH$_2$— has the same structure as the side-chain from the amino acid arginine while H$_2$N—(CH$_2$)$_4$— has the same structure as the side-chain from the amino acid lysine.

Generally, chiral carbon atoms in the compounds of Formula I, II or III may be in either optically active R— or S— configuration. Therefore, where amino acid moieties are present in the compounds, they may have either the L- or D-configurations. Optically pure compounds, racemic mixtures, and diastereomeric mixtures are all contemplated within the scope of the invention.

Pharmaceutically acceptable salts encompass any salts of the active compounds which are suitable for the formulation of a pharmaceutical composition and which are compatible with the animal to which the compound is being administered. Such salts include, but are not limited to, salts of acids (e.g. hydrochlorides and sulphates) and salts of bases (e.g. sodium and ammonium salts).

For the synthesis of cyclic peptides (Formula I), Kaiser's oxime-resin may be used following the procedures of Nishino et al. (*J. Chem. Soc., Perkin Trans.* 1, 1996, 939–946) and Osapay et al. (*Tetrahedron Lett.* 1990, 31, 6121–6124), the disclosures of which are hereby incorporated by reference.

The solid-phase synthesis of the compounds of Formula II or III (Schemes 2a and 2b) may be achieved by starting with MBHA Resin (i.e. modified Merrifield resin, which is a polystyrene based resin having bound thereto a 4-methyl-benzhydrylamine hydrochloride moiety) or with Rink-Amide Resin. The method may begin with neutralization of the amine hydrochloride group in MBHA resin (1) with 10% N,N'-diisopropylethylamine/$CH_2Cl_2$ (DIEA/DCM) or with the removal of the Fmoc-protecting group from Rink-Amide resin (2) with 20% piperidine in DMF. Protected N-amino acids may then be attached to the resultant amino-resin (method A or method B) or to 4-sulfamylbutyryl AM resin (3) (method C) using benzotriazole-1-yl-oxy-tris-pyrrolidino-phosphonium hexafluorophosphate (PyBOP/DIEA). The intermediates 4, 5, 6 are ninhydrin negative by the Kaiser test (Kaiser et al. *Anal. Biochem.* 1970, 34, 595–598).

Incorporation of specific groups may be achieved by reacting the deprotected resin 4, 5, 6 with a variety of substituted o-fluoro-nitroarens (preferably about 10 equiv.) and DIEA (preferably about 5 equiv.) in DMF or DMSO, preferably for about 2 days (Scheme 2b). The completion of the reaction leading to substituted o-nitro-aniline resin (7) may be monitored by the ninhydrin test.

In the next step, the aryl nitro group (intermediate resin product 7) may be reduced by a solution (preferably at a concentration of about 1 M) of tin(II) chloride dihydrate ($SnCl_2.2H_2O$) in N-methylpyrrolidine-2-one (NMP) in the presence of N-methylmorpholine (NMM), preferably overnight at room temperature. The resin may be washed and then immediately acylated by using symmetric anhydride generated in situ from N',N'-dicyclohexylcarbodiimide (DCC) and corresponding carboxylic acids (path a in scheme 2b) or treated with aldehydes in NMP, preferably for about 8 hr at room temperature, followed by heating, preferably at about 50° C. for about 8 hr (path b in scheme 2b).

Resin-bound o-(N-acyl)-phenylenediamine (8) or benzimidazole (9) may be washed with DMF, MeOH, DCM and $Et_2O$ and then dried in vacuo overnight at room temperature. The compounds may then be cleaved from the MBHA resin with liquid hydrogen fluoride (HF) under standard cleaving conditions (Matsueda et al. *Peptide,* 1981, 2, 45–50, the disclosure of which is hereby incorporated by reference). Substituted-Rink-Amide resin may be treated with $CF_3COOH$ (TFA/$H_2O$ (95:5)), preferably for 1 hour at ice-bath temperature (Lee et al. *J. Org. Chem.* 1997, 62, 3874–3879, the disclosure of which is hereby incorporated by reference). For the removal of the compounds from the resin, the 4-sulfamylbutyryl AM resin may first be N-methylated with $ICH_2CN$/DIEA in NMP and then treated with either hydroxide at room temperature or an amine in THF or dioxane at elevated temperature (Backes et al. *J. Am. Chem. Soc.,* 1996, 118, 3055–3056, the disclosure of which is hereby incorporated by reference).

Scheme 2a:

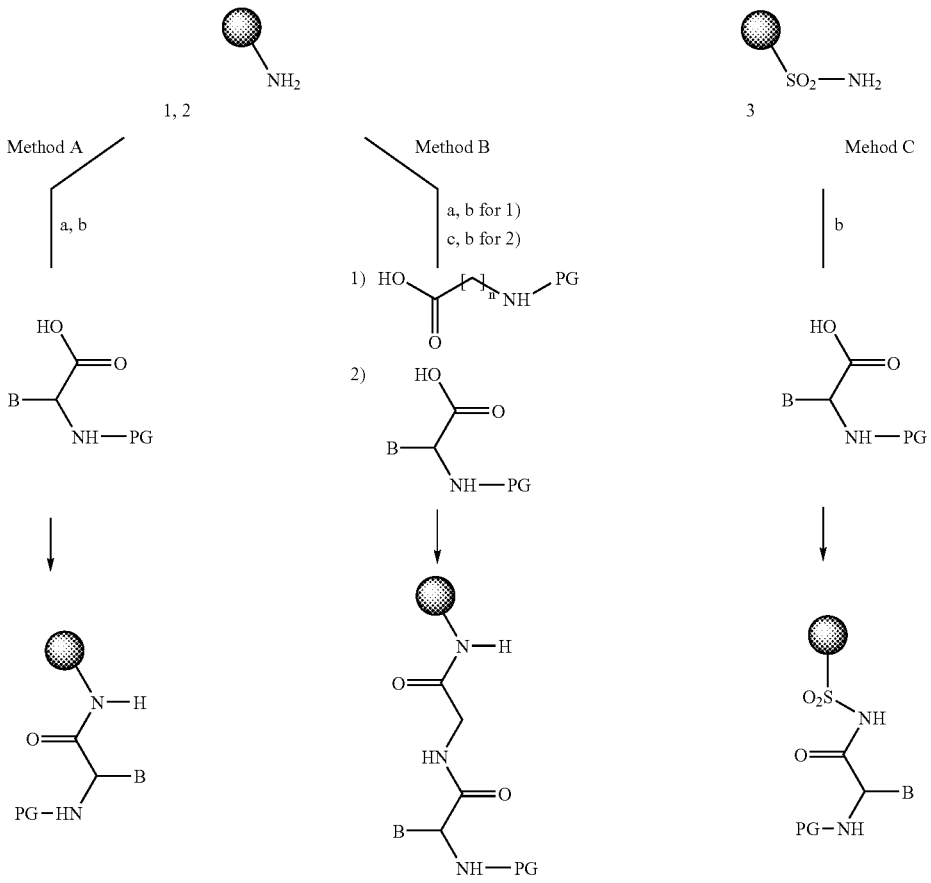

(PG: protecting group; B: as defined underneath;
a: 10% DIEA in DCM or 20% piperidine in DMF;
b: PyBOP/DIEA; c: 40% TFA in DCM or 20% piperidine in DMF)

Scheme 2b:

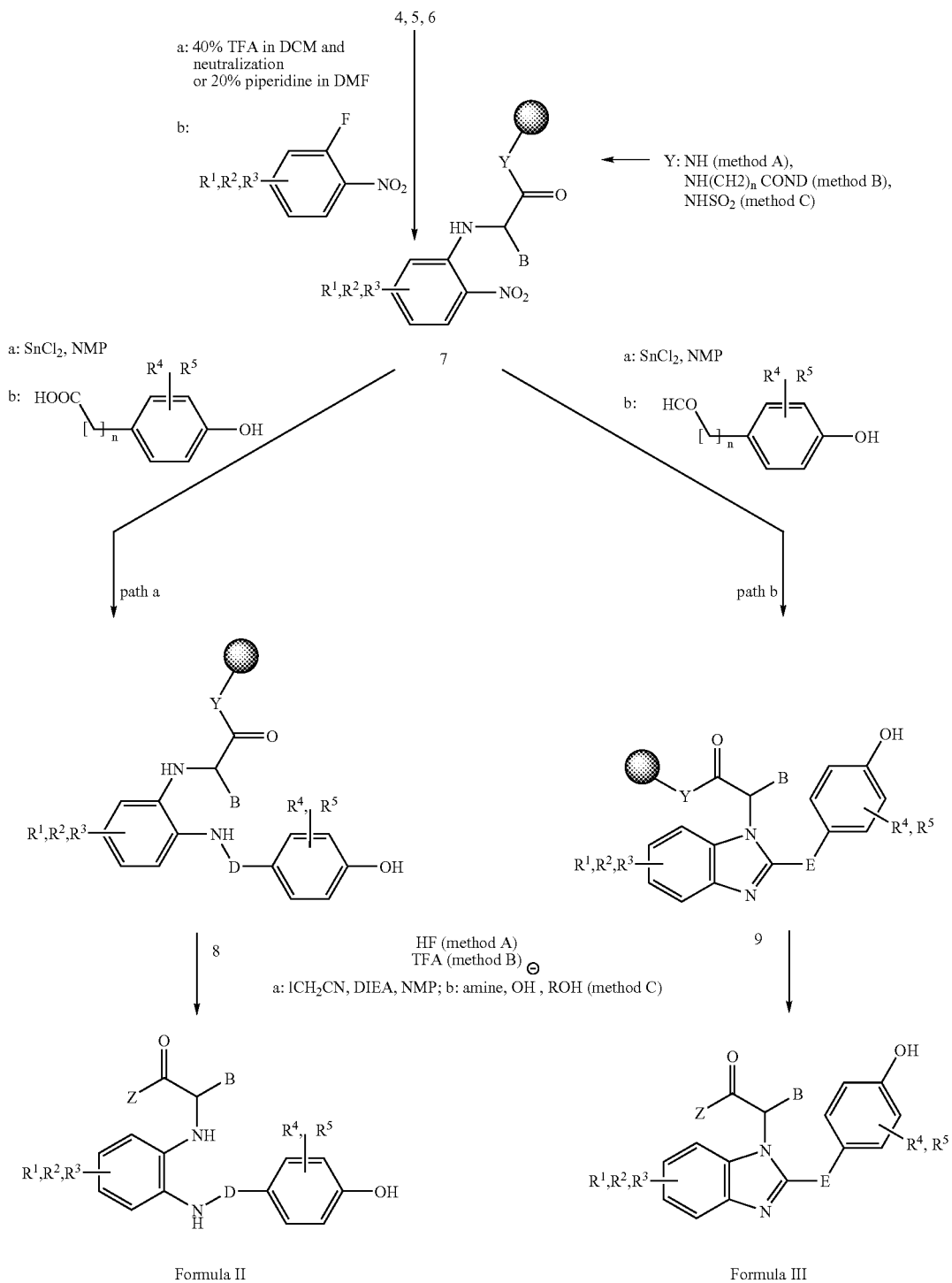

wherein B, D, E, $R^1$, $R^2$, $R^3$, $R^4$, R and Z represent the groups described above and the spherical element in Schemes 2a and 2b represents the remainder of the MBHA resin, Rink-Amide resin or 4-sulfamylbutyryl AM resin, as appropriate.

Particularly preferred compounds that may be prepared by the procedures described above are:

(A) Cyclic tetrapeptides of Formula I (see Scheme 3):

Cyclo(-Gly-(p-chloro)Phe-Tyr-D-Ala-) [Compound I-1] (SEQ ID NO. 5)

Cyclo(-Gly-(p-chloro)Phe-Tyr-(p-amino)
Phe-)                    [Compound I-2] (SEQ ID NO. 6)

Cyclo(-Gly-(p-chloro)Phe-Tyr-(p-guanidino)
Phe-)                    [Compound I-3](SEQ ID NO. 7)

Cyclo(-Gly-(p-amino)Phe-Tyr-D-
Arg-)                    [Compound I-4](SEQ ID NO. 8)

Cyclo(-Thr-(p-chloro)Phe-Tyr-D-
Arg-)                    [Compound I-5] (SEQ ID NO. 9)

(B) Non-peptides of Formula II (see Scheme 4):

N-5-guanidinopentanamide-(2S)-yl-2-N-(p-hydrox-
yphenylacetyl) phenylenediamine        [Compound II-1]

N-5-guanidinopentanamide-(2S)-yl-2-N-(p-hydrox-
yphenylacetyl)-4-trifluorometyl-phenylenedi-
amine                                   [Compound II-2]

N-5-guanidinopentanamide-(2R)-yl-2-N-(p-hydrox-
yphenylacetyl)-4-carboxy-phenylenediamine  [Compound II-3]

N-5-guanidinopentanamide-(2R)-yl-2-N-(p-hydrox-
yphenylacetyl)-4-(p-chlorobenzoyl)-phenylene-
diamine                                 [Compound II-4]

(C) A non-peptide of Formula III (see Scheme 4):

N-5-guanidinopentanamide-(2R)-yl-2-(p-hydroxyben-
zyl)-5-carboxybenzimidazole             [Compound III-1]

Scheme 3:

I-1 (SEQ ID NO.5)

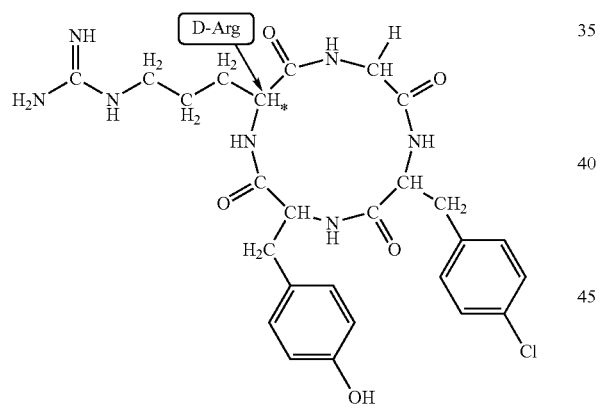

I-2 (SEQ ID NO.6)

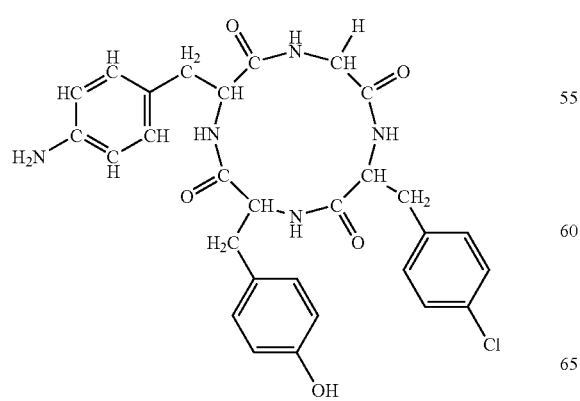

I-3 (SEQ ID NO.7)

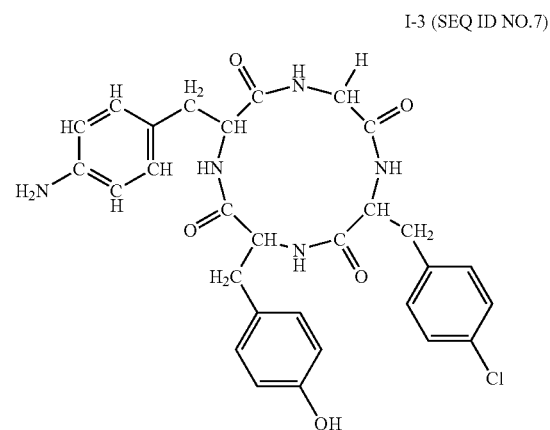

I-4 (SEQ ID NO.8)

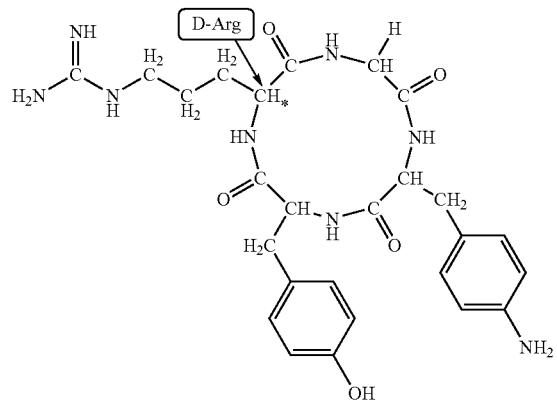

I-5 (SEQ ID NO.9)

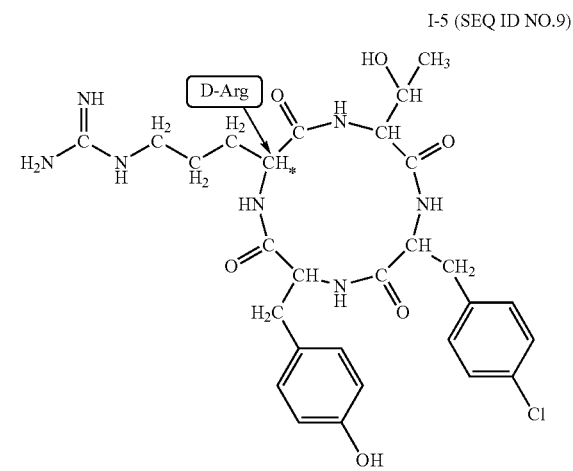

Scheme 4:

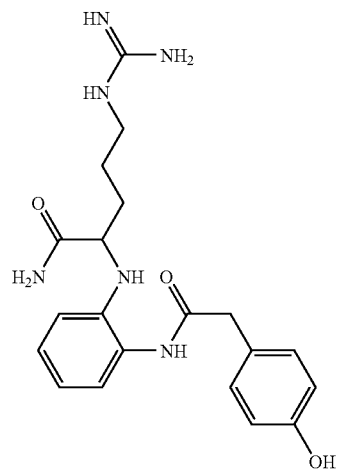

II-1

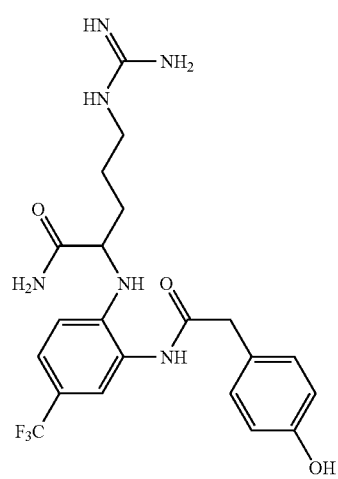

II-2

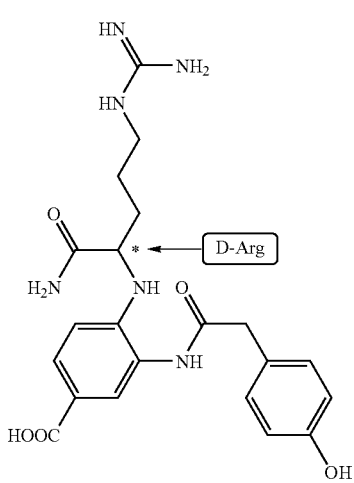

II-3

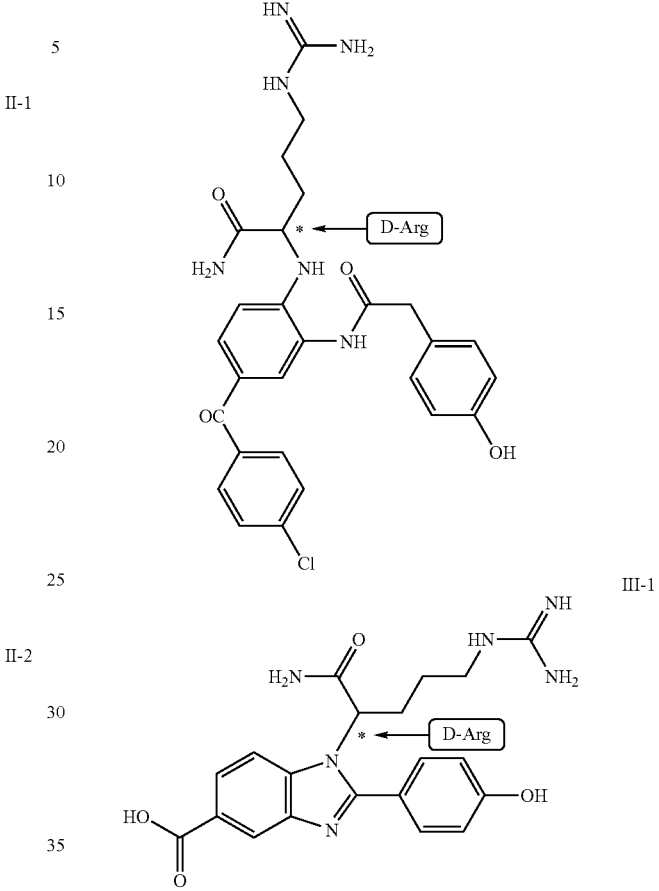

II-4

III-1

Pharmaceutical compositions comprising a compound of the present invention, or a pharmaceutically acceptable salt thereof, in admixture with a pharmaceutically acceptable carrier, diluent or excipient may be formulated by methods generally known in the art. The preparation and administration of pharmaceutical compositions are generally known in the art, for example as described in U.S. Pat. No. 5,169,833, the disclosure of which is hereby incorporated by reference.

Thus, the active compounds of the invention may be formulated for oral, buccal, transdermal (e.g., patch), intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); filters (e.g., lactose, microcrystalline cellulose or calcium phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration the composition may take the form of tablets of lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

The active compounds or pharmaceutical compositions thereof are generally administered to or used in animals, for example in humans for medical purposes or in domestic animals or farm animals for veterinary purposes. Preferably, the animal is a mammal, particularly a human. Selection of appropriate doses would depend on the particular patient and on the compound being used and is ultimately decided by a medical practitioner. Generally, doses may range, depending on the compound, from 200 times less to 500 times more than would be used for morphine, which could be administered, for example, 1 to 4 times per day.

The active compounds of the present invention are analgesic in various animal pain assays, particularly after central (i.c.v., i.t.) or peripheral (oral, i.p. and/or i.v.) administrations. They also potentiate the action of morphine, therefore, pharmaceutical compositions comprising the active compounds of the present invention in admixture with morphine are contemplated within the scope of the invention. The active compounds may be administered in conjunction with morphine to enhance the effectiveness of morphine.

The active compounds also block morphine tolerance and, particularly in isolated rat alveolar macrophages, they inhibit the induction of COX-2 and the secretion of $PGE_2$ in response to lipopolysaccharide (LPS).

The active compounds show potent analgesic activity (1.4 to 135 fold as potent as HN (SEQ ID NO. 1)) in the mouse writhing test. Significant analgesic activity is observed after both central (i.c.v.) and peripheral (oral, i.p.) administrations of compounds I-1 (SEQ ID NO. 5), II-1 and III-1. The various compounds also display high analgesic activity in the mouse tail-flick (i.c.v.) pain assay. None of the compounds (i.c.v.) induce motor dysfunction at analgesic doses as assessed by the mouse rotarod assay. In addition, compound II-1 potentiates the analgesic effects of morphine in the mouse writhing test and inhibits morphine tolerance in the mouse tail-flick assay. In isolated rat alveolar macrophages, the active compounds potently inhibit the induction of COX-2 and the secretion of $PGE_2$ in response to LPS.

BRIEF DESCRIPTION OF THE DRAWINGS

The invention will now be particularly described by non-limiting examples having reference to the appended drawings in which.

EXAMPLES

Figure 1:
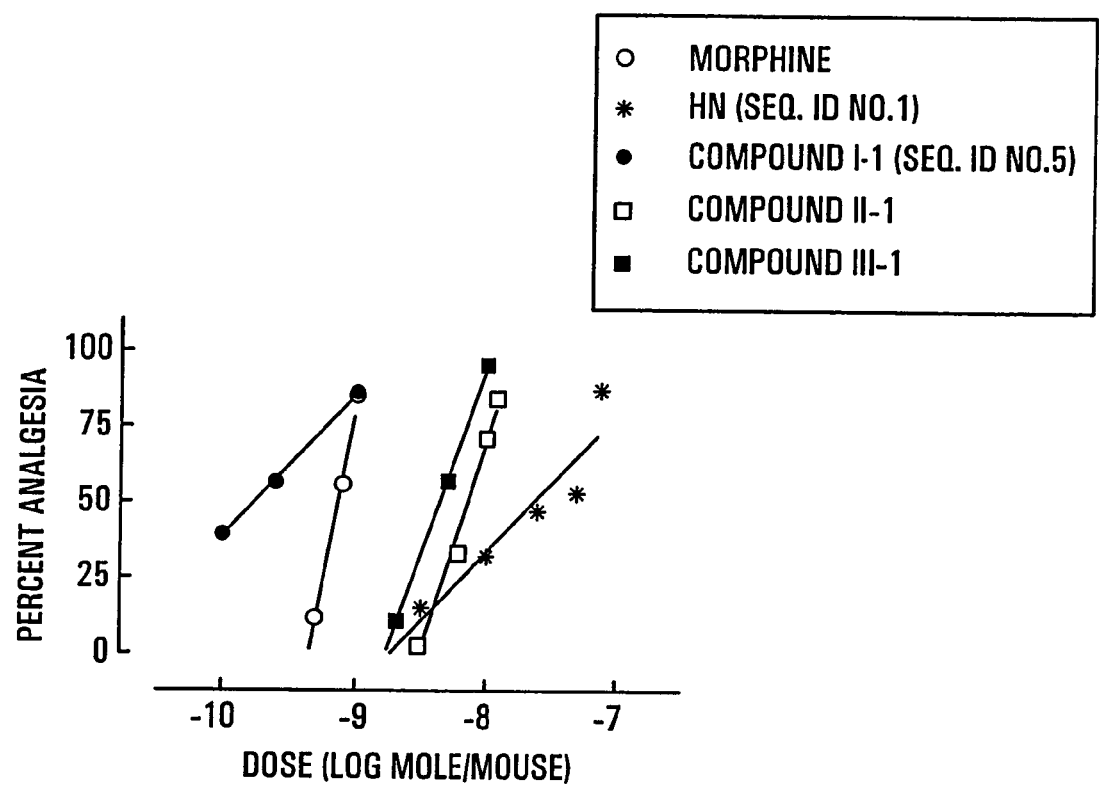
FIG. 1 is a graph showing the dose-dependent analgesic effects of morphine and Histogranin-like peptides and non-peptides (i.c.v.) in the mouse writhing assay.

The purity and identity of the synthetic products were confirmed by thin-layer chromatography, analytical HPLC on μ-Bondapak™ C-18 (Waters™) and FAB mass spectroscopy.

Example I

Cyclo(-Gly-(p-chloro)Phe-Tyr-D-Arg-) (I-1) (SEQ ID NO. 5)

Boc-Gly-oxime-resin was first prepared by mixing oxime-resin (available from Novabiochem™) (1.5g, 0.57 meq/g) with Boc-Gly-OH (1.3 g, 9 eq) in the presence of DCC (9.9 ml of DCC 8%, 4.5 eq), 4-dimethylaminopyridine (DMAP), (0.3 g, 3 eq), N-hydroxybenzotriazole hydrate (HOBt), (0.4 g, 3 eq) in 50 ml of DCM at room temperature for 12 hr. The resin was submitted to three washes with 50 ml of DCM, one wash with 50 ml of propanol-2 and two washes with 50 ml of DCM. The free oxime groups were capped by acetylation with acetic anhydride (0.4 ml, 5 eq) for 30 min. The peptide chain was then assembled according to the following coupling steps:(i) one wash with 25% trifluoroacetic acid (TFA)-DCM; (ii) deprotection with 25% TFA-DCM (30 min); (iii) two washes with DCM; (iv) one wash with propanol-2; (v) three washes with DCM; (vi) one wash with dimethylformamide (DMF); (vii) coupling of Boc-amino-acids (consecutively Boc-D-Arg(Tos)-OH (1.1 g, 3 eq), Boc-Tyr(2,6-di-Cl-Bzl)-OH (1.1 g, 3 eq) and Boc-Phe (pCl)—OH (0.8g, 3 eq)) in presence of PyBOP, (1.3 g, 3 eq), HOBt (0.13 g, 1 eq) and DIEA (0.95 ml, 6.5 eq) in DMF (45 min); (viii) three washes with DMF; (ix) two washes with DCM. Solvent volumes were 15 cm$^3$ g$^{-1}$ resin. Coupling efficiency was checked at each coupling cycle by the Kaiser test. The peptide was cleaved from the resin by intrachain aminolysis in the presence of AcOH (0.097 ml, 2 eq) and DIEA (0.293 ml, 2 eq) in 30 ml DMF at room temperature for 24 hr. The product was obtained from the solution phase by filtration. Protecting groups were removed with anhydrous hydrogen fluoride (HF) at 0° C. for 30 min. The product was purifed by chromatography on Sephadex™ G-10 (1.5 ×30 cm column) and preparative reversed-phase HPLC on μBondapak C18 column (25×100 mm) with a gradient of 0%–50% acetonitrile in 0.1% TFA and a flow rate of 5 ml/min over 65 min. The procedure yielded 50 mg of I-1 (SEQ ID NO. 5) (Scheme 3; 11% based on starting resin).

Other cyclic peptides (Scheme 3) were prepared according to this technique with the following yields: cyclo(-Gly-(p-chloro)Phe-Tyr-(p-amino)Phe-) (I-2 (SEQ ID NO. 6); 45 mg, 9%), cyclo(-Gly-(p-chloro)Phe-Tyr-(p-guanidino)Phe-) (I-3 (SEQ ID NO. 7); 15 mg, 2%), cyclo(-Gly-(p-amino)Phe-Tyr-D-Arg-) (I-4 (SEQ ID NO. 8); 40 mg, 9%), cyclo(-Thr-(p-chloro)Phe-Tyr-D-Arg-) (I-5 (SEQ ID NO. 9); 40 mg, 9%).

Example II

Synthesis of N-5-guanidinopentanamide-(2S)-yl-2-N-(p-hydroxyphenylacetyl) phenylenediamine (II-1)

Attachment of Boc-L-Arg(Tos)-OH to MBHA-resin. The MBHA-resin (1g, 0.67 mmol, Novabiochem™) was first neutralized with 10% DIEA in DCM (two 5 min washes with 50 ml each) and washed six times with six 50 ml fractions of DCM. The first amino acid was attached by mixing the resin for 1 hr at room temperature with 1.1 g (2.68 mmol) of Boc-L-Arg(Tos)-OH, 1.4g (2.68 mmol) of PYBOP, 0.2 g (1.34 mmol) of HOBt, H$_2$O and 0.9 ml (5.36 mmol) of DIEA in 50 ml of DMF/DCM (1:1). At the end of the coupling reaction, the resin was ninhydrin negative by the Kaiser test. The resulting mixed Boc-Arg(Tos)-MBHA-resin was washed three times with 50 ml of DMF, three times with 50 ml of DCM and then acetylated for 30 min with 0.6 ml (6.7 mmol) of Ac$_2$O and 0.6 ml (3.35 mmol) of DIEA in 50 ml of DCM. The resin was washed 4 times with 50 ml of DCM, 2 times with 50 ml of MeOH, 2 times with 50 ml of DCM and dried.

Incorporation of 1-fluoro-2-nitrobenzen to Boc-L-Arg(Tos)-MBHA-resin. One g of the above-described resin (approximately 0.67 mmol) was washed with 50 ml of TFA/DCM (4:6) and subsequently deprotected for 15 min with 50 ml of TFA/DCM (4:6). The resin was washed 4 times with 50 ml of DCM, neutralized twice for 2 min each with 50 ml portions of DIEA/DCM (5:95) and washed six times with 50 ml of DCM. The next reaction was conducted by addition of 0.7 ml (6.7 mmol) of 1-fluoro-2-nitrobenzene, 0.6 ml (3.35 mmol) of DIEA and 20 ml of DMF. The suspension was allowed to mix at room temperature for 24 hr, the reagents were changed and a novel suspension was made and mixed for another 24 hr. The completion of the reaction was verified by the Kaiser test. The resin then was washed 4 times with 50 ml of DMF, 2 times with 50 ml of MeOH, 2 times with 50 ml of DCM and acetylated for 30 min with 0.6 ml (6.7 mmol) of Ac$_2$O and 0.6 ml (3.35 mmol) of DIEA in 50 ml of DCM. The o-nitroaniline-resin was washed 4 times with 50 ml of DCM, 2 times with 50 ml of MeOH, 2 times with 50 ml of DCM and dried.

N-5-guanidinopentanamide-(2S)-yl-2-N-(p-hydroxyphenylacetyl) phenylenediamine (II-1). One g (approximately 0.67 mmol) of the o-nitroaniline-resin was reduced with 1 M of SnCl$_2$, 2H$_2$O (4.5 g) and 1 M of NMM (2.2 ml) in 20 ml of NMP overnight at room temperature. The resin was washed 4 times with 50 ml of NMP, 2 times with 50 ml of DCM, 2 times with 50 ml of MeOH, 2 times with 50 ml of DCM and then immediately acylated with 0.18 M of carboxylic anhydride prepared in situ from 1 g (6.7 mmol) of 4-hydroxyphenylacetic acid, 17.3 ml (6.7 mmol) of 8% DCC/DCM, 0.5 g (3.35 mmol) of HOBt.H$_2$O and 0.4 g (3.35 mmol) of DMAP in 20 ml DCM overnight at room temperature. The resin was washed with 50 ml portions of DMF (×4), DCM (×2), MeOH (×2), DCM (×2), Et$_2$O (×2) and dried in vacuum. Compound (II-1) was cleaved from the resin by treatment with 15 ml of anhydrous liquid HF and 1 ml of anisole as scavenger for 1 hr at 0° C. HF and scavenger were evaporated in vacuo. The compound was extracted from the dried resin with 50 ml of DMF (×4), and then concentrated in vacuo. It was purified by gel filtration on Sephadex™ G-10 followed by preparative reversed-phase HPLC using a 25×200 mm column (Water, μ-Bondapak C18, 10 μm, 125 Å), operating at a flow 5 ml/min. The chromatography was achieved using a gradient of acetonitrile in 0.1% TFA, increasing from 15% to 65% over 1 hr. The purified compound was detected by UV at 280 nm. Yield: 120 mg (45%) (based on the substitution of the starting resin).

Example III

N-5-guanidinopentanamide-(2S)-yl-2-N-(p-hydroxyphenylacetyl)-4-trifluorometyl-phenylenediamine (II-2). The preparation of compound II-2 was performed as described above. 4-fluoro-3-nitrobenzotrifluoride was used instead of 1-fluoro-2-nitrobenzen in the 2$^{nd}$ step. 1 g of the deprotected H-L-Arg(Tos)-MBHA-resin (approximately 0.67 mmol) was added 0.9 ml (6.7 mmol) of 4-fluoro-3-nitrobenzotrifluoride, 0.6 ml (3.35 mmol) of DIEA and 20 ml of DMF. The suspension was allowed to mix at room temperature for 24 hr, followed by a change of the reagents and another 24 hr of mixing. The completion of the reaction was verified by the Kaiser test. The other steps were accomplished using the same reaction conditions as those described for compound II-1. Yield: 96 mg (31%).

Example IV

N-5-guanidinopentanamide-(2R)-yl-2-N-(p-hydroxyphenylacetyl)-4-carboxyphenylene-diamine (II-3). Compound II-3 was obtained following a procedure similar to that used for the preparation of compound II-1. Boc-D-Arg(Tos)-OH was used instead of Boc-L-Arg(Tos)-OH in the 1$^{st}$ step and 4-fluoro-3-nitrobenzoic acid was used in the 2$^{nd}$ step. One g of the MBHA-resin (0.67 mmol) was coupled with 1.1 g (2.68 mmol) of Boc-D-Arg(Tos)-OH, 1.4g (2.68 mmol) of PyBOP, 0.2 g (1.34 mmol) of HOBt.H$_2$O and 0.9 ml (5.36 mmol) of DIEA in 50 ml of DMF/DCM (1:1) for 1 hr at room temperature. In the $2^{nd}$ step, 1 g of the deprotected H-L-Arg(Tos)-MBHA-resin (approximately 0.67 mmol) was added 1.2 g (6.7 mmol) of 4-fluoro-3-nitrobenzoic acid, 0.6 ml (3.35 mmol) of DIEA and 20 ml of DMF. The suspension was allowed to mix at room temperature for two 24 hour periods as described above. The other steps were accomplished in the same reaction conditions as those for compound II-1. Yield: 90 mg (30%).

Example V

N-5-guanidinopentanamide-(2R)-yl-2-N-(p-hydroxyphenylacetyl)-4-(p-chlorobenzoyl)-phenylenediamine (II-4). Compound II-4 was obtained following a procedure similar to that used for the preparation of compound II-3. Following acetylation of amino group with 4-hydroxyphenylacetic anhydride prepared in situ from DCC and corresponding carboxylic acid, 1 g (approximately 0.67 mmol) of the resin-bound o-(N-acyl) phenylenediamine was treated with 1.1 g (6.7 mmol) of 1,1'-carbonyldiimidazole and 0.4 g (3.35 mmol) of DMAP in 20 ml of tetrahydrofuran (THF) overnight at 4° C. then immediately coupled with 6.7 ml (6.7 mmol) of 4-chlorophenylmagnesium bromide (1.0 M solution in diethyl ether) in 20 ml of THF overnight at 4° C. The other steps were accomplished using the same reaction conditions as those described for compound II-3. Yield: 49 mg (14%).

Example VI

N-5-guanidinopentanamide-(2R)-yl-2-(p-hydroxybenzyl)-5-carboxybenzimidazole (III-1). Compound III-1 was obtained by a modification of the procedure for the preparation of compound II-3. Following the reduction of nitro group with $SnCl_2 \cdot 2H_2O$, 1 g (approximately 0.67 mmol) of the o-aminoaniline-resin was immediately treated with 0.8 g (6.7 mmol) of p-hydroxybenzaldehyde in NMP with stirring for 8 hr at room temperature, followed by heating at 50° C. for 8 hr. The resultant resin was transferred to a 25 ml filter tube, washed with the following schedule (50 ml each): NMP (×3), DCM (×2), MeOH (×3), $Et_2O$ (×3). It was then dried overnight in vacuo at room temperature. Finally, the cleavage and purification steps were accomplished using the same conditions as those described for compound II-3. Yield: 94 mg (34%).

The purity and identity of the synthetic compounds were assessed by thin layer chromatography (TLC), high performance liquid chromatography (HPLC) and mass spectrometry (ES-MS or FAB-MS) (Table 1).

TABLE 1

Analytical properties of Histogranin-like peptides and non-peptides.

| Compounds | TLC (Rf)[a] | HPLC (k')[b] | ES-MS or FAB-MS (MH+) |
|---|---|---|---|
| Peptides | | | |
| I-1 (SEQ ID NO. 5) | 0.77 | 4.47 | 558 |
| I-2 (SEQ ID NO. 6) | 0.86 | 4.00 | 580 |
| I-3 (SEQ ID NO. 7) | 0.58* | — | 622 |
| I-4 (SEQ ID NO. 8) | 0.52 | 4.19 | 538 |
| I-5 (SEQ ID NO. 9) | 0.65 | 0.83 | 602 |

TABLE 1-continued

Analytical properties of Histogranin-like peptides and non-peptides.

| Compounds | TLC (Rf)[a] | HPLC (k')[b] | ES-MS or FAB-MS (MH+) |
|---|---|---|---|
| Peptides | | | |
| Non-peptides | | | |
| II-1 | 0.66 | 2.02 | 399 |
| II-2 | 0.70 | 2.18 | 467 |
| II-3 | 0.68 | 0.70 | 443 |
| II-4 | 0.70 | 1.54 | 538 |
| III-1 | 0.59 | 2.50 | 411 |

[a]BAWP (v/v), 1-butanol-acetic acid-water-pyridine (15/3/10/12).
[b]by analytical reversed-phase HPLC using a 3.9 × 300 mm column (Water, μBondapak ™ C18), operating at a flow 1 ml/min. Separations were achieved using a water/acetonitrile/TFA gradient, increasing from 0% to 50% (I-1, I-2), 0% to 65% (I-4, I-5), 15% to 65% (compounds II-1 and II-2) and from 15% to 80% (compounds II-3, II-4 and III-1) over 50 min and UV detection at 280 and 350 nm.
*$R_f$ (v/v, $CH_2Cl_2$/MeOH, 8/2).

Example VII

Analgesia, Morphine Potentiation and Blockade of Morphine Tolerance

Materials and Methods:

Animals. Mice (male 20–25 g, Swiss Webster) were obtained from Charles River (Canadian Breeding Farm, St. Constant, Quebec). They were housed five per cage in a room with controlled temperature (22±2° C.), humidity and artificial light (06.30–19h). The animals had free access to food and water and were used after a minimum of 4 days of acclimation to housing conditions. Experiments were carried out between 10:00 a.m. and 4:00 p.m. in an air-regulated and soundproof laboratory (23±1° C., 40% humidity), in which mice were habituated at least 30 min before each experiment. The experiments were authorized by the animal care committee of the University of Ottawa in accordance with the guidelines of the Canadian Council on Animal Care.

Drugs and peptides. Morphine, raclopride, naloxone, SCH-23390 were products of ENDO laboratory Inc (Garden City, N.Y.). HN (SEQ ID NO. 1), [$Ser^1$]HN, HN-(7–15) (SEQ ID NO. 4) and H4-(86–100) (SEQ ID NO. 2) were synthesized by the solid-phase procedure (Lemaire et al. Int. J. Peptide Protein Res. 1986, 27, 300–305). Cyclic tetrapeptides and non-peptides were synthesized as described above.

Administration of compounds. The i.c.v. administrations of the peptides and non-peptides in mice were performed as described by Shukla et al. (Shukla et al., Brain Res. 1992, 591,176). Peptides are dissolved in double-distilled sterile water (vehicle) and 10 μl of the peptide solution or vehicle are delivered gradually within approximately 3 sec, mice exhibiting normal behaviour within 1 min after injection. The administration site is confirmed by injecting Indian ink in preliminary experiments.

Mouse writhing test. Antinociceptive activity of HN (SEQ ID NO. 1) and related compounds were evaluated using the acetic acid-induced writhing test according to a modification (Shukla et al., Brain Res. 1992, 591,176) of the method of Hayashi and Takemori (Eur. J. Pharmacol. 1971, 16, 63). Male swiss webster [(SW)f BR] mice are injected intraperitoneally (i.p.) with 1.0% acetic acid (10 ml/kg) 5 min after i.c.v. injection of 0 (saline), 0.1, 0.5, 1, 10, 25, 50, 75 and 100 nmol of HN (SEQ ID NO. 1) or related peptides or non-peptides. The number of writhes displayed by each mouse is counted for a period of 10 min after the injection of the acetic acid solution. An abdominal stretch is characterized by the contraction of the abdominal muscles, the arching of the back ventrally such as the abdomen touches the bedding surface and the extension of one or both hind limbs. Mice are used once and then killed immediately. Groups of 10 mice are used for each dose. The analgesic activity of the peptides is assessed by the percent analgesia displayed by a test group of 10 mice. The percentage of analgesia is calculated for each dose by the formula: [(mean number of writhes in control group —mean number of writhes for the test group)/(mean number of writhes in control group)×100]. The doses producing 50% analgesia ($AD_{50}$) with 95% confidence limits (95% CL) and potency ratios with 95% CL are measured by the method of Lichfield and Wilcoxon (J. Pharmacol. Exp. Ther. 1949, 96, 99–104) using procedure 47 of the computer program of Tallarida and Murray (in "Manual of pharmacological calculations with computer programs". 2nd ed., Springer, N.Y., 1987).

In order to determine the length of action of the compounds, the acetic acid solution is administered at different times after the administration of the drug, as indicated. The experiments for the assessment of the peripheral-antinociceptive activity of the compounds are performed by administration of 10 or 20 µmol/kg i.p or i.v. or 0.5 or 1 mg /mouse oral of the tested compounds 30 and 60 min prior to the injection of the acetic acid solution. Data are analyzed by the Wilcoxon's paired non-parametric test. The criterion for statistical significance was P<0.05.

Mouse tail flick assay. Antinociception was also determined using the radiant heat tail-flick technique (D'Amour and Smith, J. Pharmacol. Exp. Ther. 1941, 72: 74). Briefly, the latency to withdraw the tail from a focused light stimulus was determined using a photocell. The light intensity was set to give a control reading of about 3 sec. Baseline latencies were determined before experimental treatment as the mean of two trials and a maximal latency of 12 s was used to minimize tissue damage. Post-treatment latencies were determined 5 min after i.c.v. injection. The antinociceptive effect was expressed as the percentage of the maximum possible effect, as calculated by the formula: % MPE=[(post-injection latency-baseline latency)/(cutoff latency-baseline latency)]×100. The use of % MPEs takes into account differences in baseline latencies so that these differences do not bias the quantification of antinociception. Group % MPE means were compared using one-way ANOVAs and $P \leq 0.05$ was considered significant.

The induction of tolerance to morphine was obtained as described by Verma and Kulkarni (Eur. J. Neuropsychopharmacol. 1995, 5, 81–87). Briefly, groups of 10 mice were injected i.p. for 8 consecutive days twice a day at 9.00 and 17.00 hr with saline, morphine (10 mg/kg), II-1 (4 mg/kg) or a combination of II-1 (4 mg/kg) 30 min prior to morphine (10 mg/kg). Tail-flick latency to thermal pain was recorded 30 min after the i.p. administration(s) in the morning session of days 1, 3, 6 and 8 as indicated in the figure.

Mouse rotarod assay. The rotarod treadmill (model 7600, UGO Basile, Italy) for mice was used to assess the motor side-effects of antinociceptive agents. The method used is derived from the procedure described by Dunham and Miya (J. Am. Pharmac. Assoc. 1957, 46: 208). The apparatus is constituted of a rod with a diameter of 2.5 cm suspended horizontally 50 cm above a plane working area. The rod is turning at a speed of 8 revolutions per min. Circular perpex separators are placed at regular intervals along the rod so that five mice can be tested at the same time. Before administering any compound, all animals are placed on the turning rod for one min in two consecutive rounds. Mice that fall from the rod during these conditioning experiments are excluded from the assay. For the assay, the test compounds were administered i.c.v. and the animals were placed on the turning rod for two min. The % of mice in groups of 10 mice which fell during this latter two min-experiment was recorded as the % of mice showing motor effects. Rotarod assays were conducted at different times (up to 60 min) after the administration of peptides. Statistical calculation were made using Student t-test.

Results:

Mouse writhing pain assay. Histogranin (HN) (SEQ ID NO. 1) and related peptides and non-peptides were tested for their abilities to block writhing in mice induced by intraperitoneal administration of acetic acid. All compounds (i.c.v.) blocked writhing in a dose-dependent manner (FIG. 1), I-1 (SEQ ID NO. 5) being 135 and 3.9 fold more potent than HN and morphine, respectively (Table 2). The non-peptides displayed potencies that were comparable to that of morphine (in the nmol range). The lengths of action of the various compounds were evaluated by measuring the time ($T_{1/2}$) it took after injection of a specific dose of a compound to produce half-maximal effect. $T_{1/2}$ of HN (SEQ ID NO. 1) (50 nmol/mouse, i.c.v.) was 22.1 min (Table 2). $T_{1/2}$ of the cyclic tetrapeptides were longer than 60 min, I-1 (SEQ ID NO. 5) displaying the longest $T_{1/2}$ (>90 min at a dose of 10 nmol/mouse). $T_{1/2}$ of the non-peptides (10 nmol) ranged between 15 and 58 min, compound II-3 showing the longest $T_{1/2}$ (58 min).

Figure 2A:
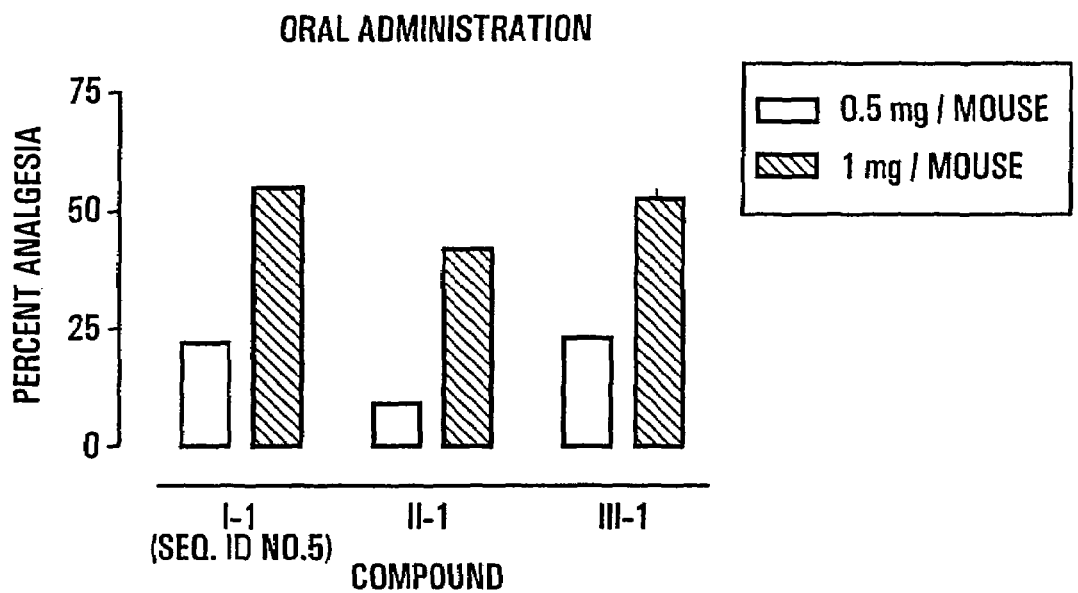
FIGS. 2A and 2B are graphs showing the antinociceptive effects of oral and intraperitoneal administrations of HN-like peptides and non-peptides in the mouse writhing test.
Figure 2B:
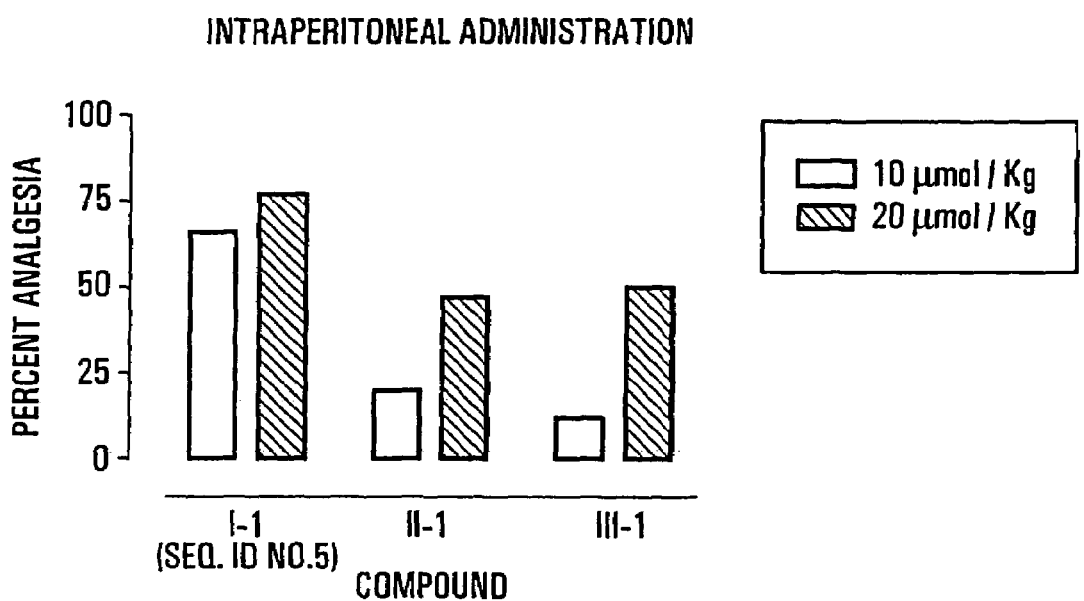

Analgesic effects of peripheral administrations. Compounds I-1 (SEQ ID NO. 5), II-1 and III-1 were shown to display dose-dependent analgesic activity in the mouse writhing test after oral and i.p. administrations (FIG. 2). Compounds I-1 (SEQ ID NO. 5), I-4, and II-1 also showed 84%, 71% and 35% analgesia, respectively, after i.v. administration (1 µmol/kg, not shown).

Figure 3:
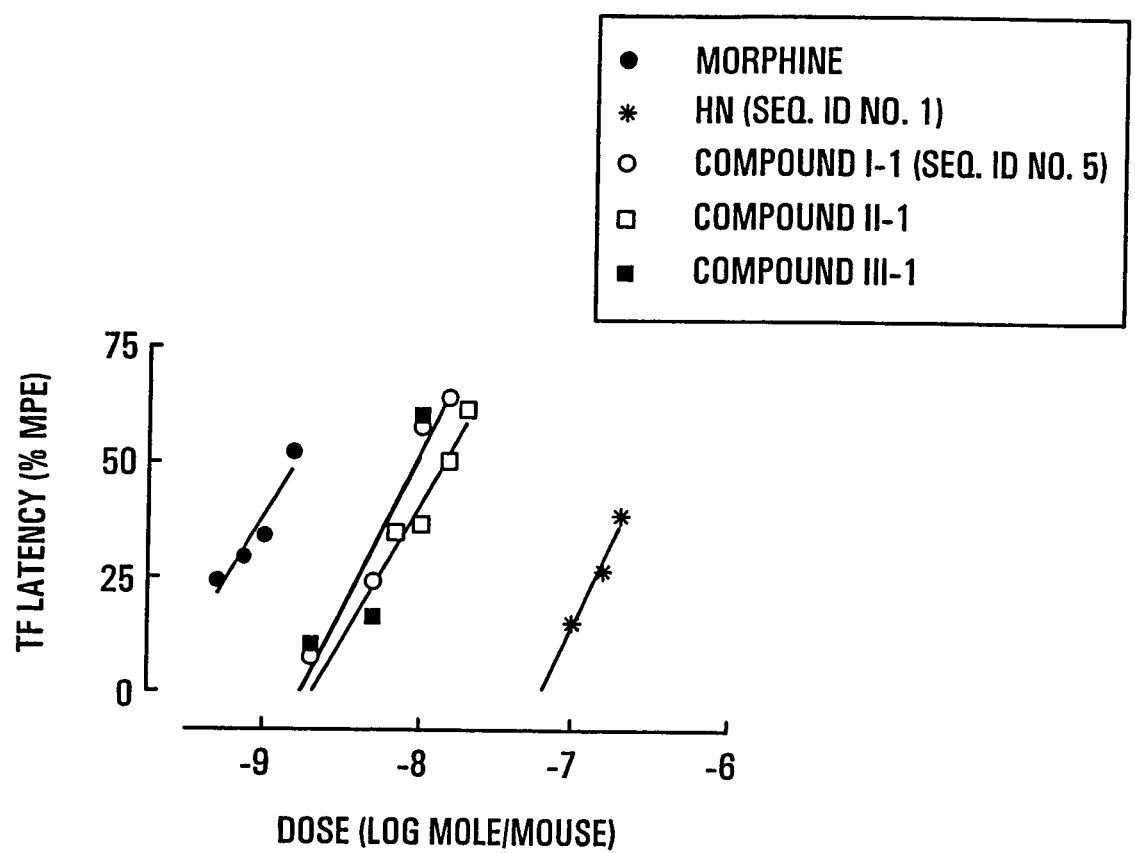
FIG. 3 is a graph showing the dose-dependent analgesic effects of morphine and Histogranin-like peptides and non-peptides in the mouse tail-flick assay.

Mouse tail-flick assay. In the mouse tail-flick assay, HN related compounds of Formulae I, II and III displayed dose-dependent analgesia (FIG. 3). All HN related compounds including compounds I-1 (SEQ ID NO. 5), II-1 and III-1 were more potent than HN (SEQ ID NO. 1) (Table 3). Compound I-1 (SEQ ID NO. 5) (10 nmol/mouse, i.c.v.) had a $T_{1/2}$ of >120 min as compared with 45 min for [Ser1]HN (50 nmol/mouse, i.c.v.).

TABLE 2

Relative potencies of Histogranin (HN) (SEQ ID NO. 1) and related peptides and non-peptides (i.c.v.) in the mouse writhing assay

| Compounds | $AD_{50}$ (nmol/mouse) (95% CL)[a] | Potency ratio[b] (95% CL)[a] | $T_{1/2}$ (min) | [dose][c] (nmol) |
|---|---|---|---|---|
| Morphine | 0.72 (0.66–0.78) | 34.8 (16.0–71.2)* | 22 | [0.5] |
| HN (SEQ ID NO. 1) | 23.0 (12.5–47.0) | 1.0 | 22.1 | [50] |
| HN-(7–15) (SEQ ID NO. 4) | 8.5 (1.9–15.4) | 2.71 (0.81–34.7)* | | |
| I-1 (SEQ ID NO. 5) | 0.17 (0.06–0.46) | 135 (27.2–783)* | >90 | [10] |
| I-2 | 6.79 | 3.39 | | |

TABLE 2-continued

Relative potencies of Histogranin (HN) (SEQ ID NO. 1) and related peptides and non-peptides (i.c.v.) in the mouse writhing assay

| Compounds | $AD_{50}$ (nmol/mouse) (95% CL)[a] | Potency ratio[b] (95% CL)[a] | $T_{1/2}$ (min) | [dose][c] (nmol) |
|---|---|---|---|---|
| (SEQ ID NO. 6) | (3.18–14.49) | (0.86–14.8)* | | |
| I-3 | 1.08 | 21.3 | >60 | [10] |
| (SEQ ID NO. 7) | (0.30–3.6) | (3.47–157)* | | |
| I-4 | 2.52 | 9.14 | | |
| (SEQ ID NO. 8) | (2.02–3.50) | (3.57–23.3)* | | |
| I-5 | 10.7 | 2.14 | | |
| (SEQ ID NO. 9) | (10.1–11.3) | (1.16–4.65)* | | |
| II-1 | 6.5 | 3.54 | 15 | [10] |
| | (4.55–9.29) | (1.82–6.87)* | | |
| II-2 | 16.1 | 1.40 | 19 | [10] |
| | (9.91–26.3) | (0.54–3.63) | | |
| II-3 | 3.16 | 7.27 | 58 | [10] |
| | (1.79–5.62) | (3.26–16.2)* | | |
| II-4 | 2.61 | 8.87 | 36 | [10] |
| | (1.53–4.48) | (4.06–19.1)* | | |
| III-1 | 4.14 | 5.56 | 36 | [10] |
| | (32.3–7.38) | (2.40–12.4)* | | |

[a]CL: confidence limit.
[b]Potency ratio relative to Histogranin (HN) (SEQ ID NO. 1).
[c]The time after injection of the compound at which half-maximal response was observed for the indicated dose.
*P < 0.05 in comparison with HN (SEQ ID NO. 1).

TABLE 3

Relative potency of Histogranin (HN) (SEQ ID NO. 1) and related peptides and non-peptides (i.c.v.) in the mouse tail-flick assay

| Compounds | $AD_{50}$ (nmol/mouse) (95% CL)[a] | Potency ratio[b] (95% CL)[a] | $T_{1/2}$ (min) | [dose] (nmol) |
|---|---|---|---|---|
| Morphine | 1.57 | 72.6 | | |
| | (1.28–1.93) | (47.6–10)* | | |
| [Ser[1]] HN | 114 | 1 | 45.0 | [50] |
| | (92–141) | | | |
| I-1 | 9.1 | 12.5 | >120 | [10] |
| (SEQ ID NO. 5) | (3.7–22.3) | (4.1–38.1)* | | |
| I-5 | 38.5 | 2.96 | 45.0 | [20] |
| (SEQ ID NO. 9) | (32.5–45.4) | (2.02–4.3)* | | |
| II-1 | 14.2 | 8.0 | 21.3 | [10] |
| | (11.5–17.4) | (5.2–12.2)* | | |
| II-2 | 98.6 | 1.16 | 18.5 | [10] |
| | (70.0–138.8) | (0.66–2.01) | | |
| II-3 | 31.7 | 3.59 | 28.9 | [10] |
| | (22.9–43.8) | (2.10–6.16)* | | |
| II-4 | 13.1 | 8.70 | 16.7 | [10] |
| | (10.6–16.1) | (5.71–13.3)* | | |
| III-1 | 9.6 | 11.9 | 28.5 | [10] |
| | (0.1–800) | (0.12–1400) | | |

[a]CL: confidence limit.
[b]Relative to [Ser[1]] HN.
*P < 0.05 in comparison with [Ser[1]] HN.

Potentiation and Prolongation of Morphine Analgesia.

Figure 4A:
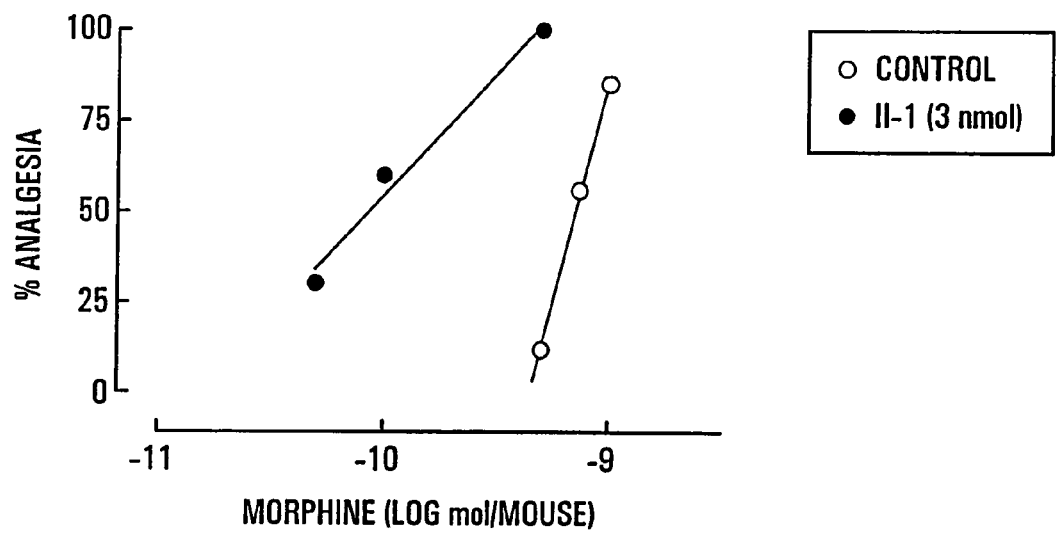
FIGS. 4A and 4B are graphs showing the potentiation (A) and prolongation (B) of the analgesic effect of morphine (i.c.v.) in the mouse writhing test by coadministration of a subanalgesic dose (3 nmol) of compound
Figure 4B:
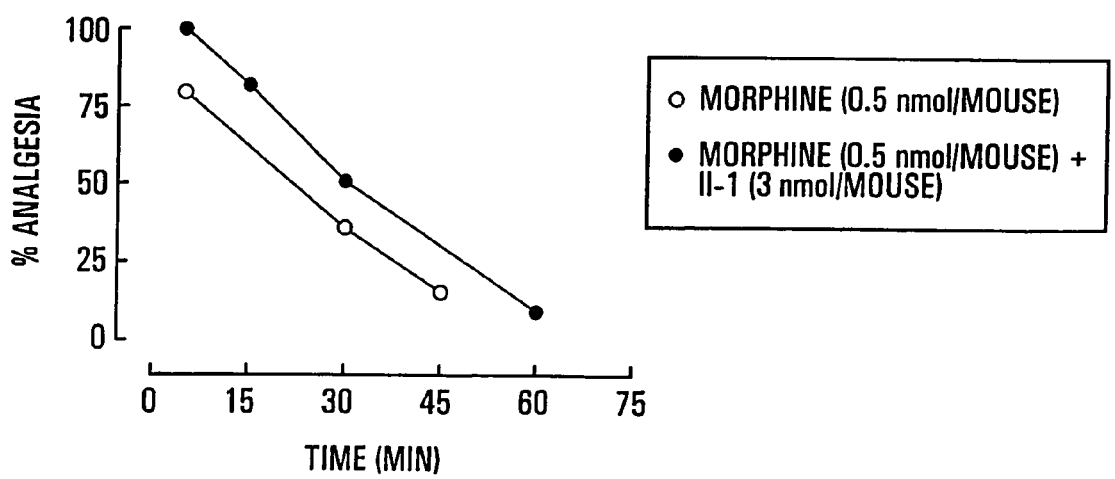

Coadministration (i.c.v.) of a subanalgesic dose of compound II-1 with morphine induced a left shift in the dose-response curve of morphine in the mouse writhing test (FIG. 4A). Similar effects were also observed with I-1 (SEQ ID NO. 5) on the dose-response curve of morphine (i.v.; not shown). The analgesic effects of morphine (0.5 nmol, i.c.v.) were also slightly prolonged by the coadministration of compound II-1 (FIG. 4B).

Figure 5:
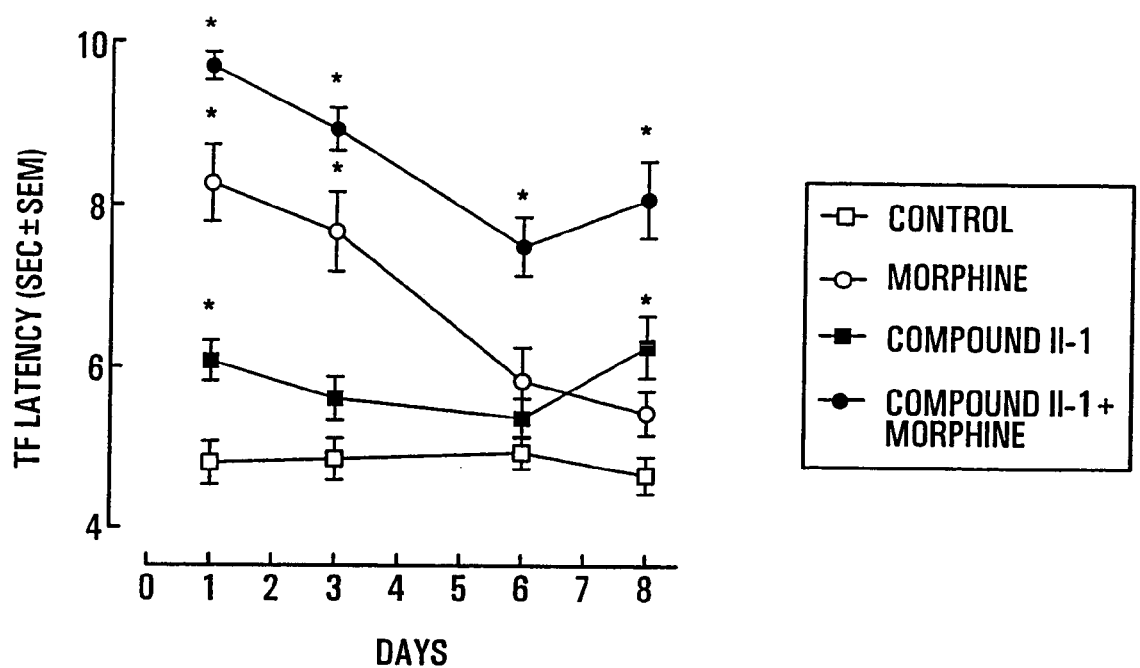
FIG. 5 is a graph showing blockade of morphine tolerance by compound II-1 in mice (*P<0.05 as compared with control).
Figure 7:
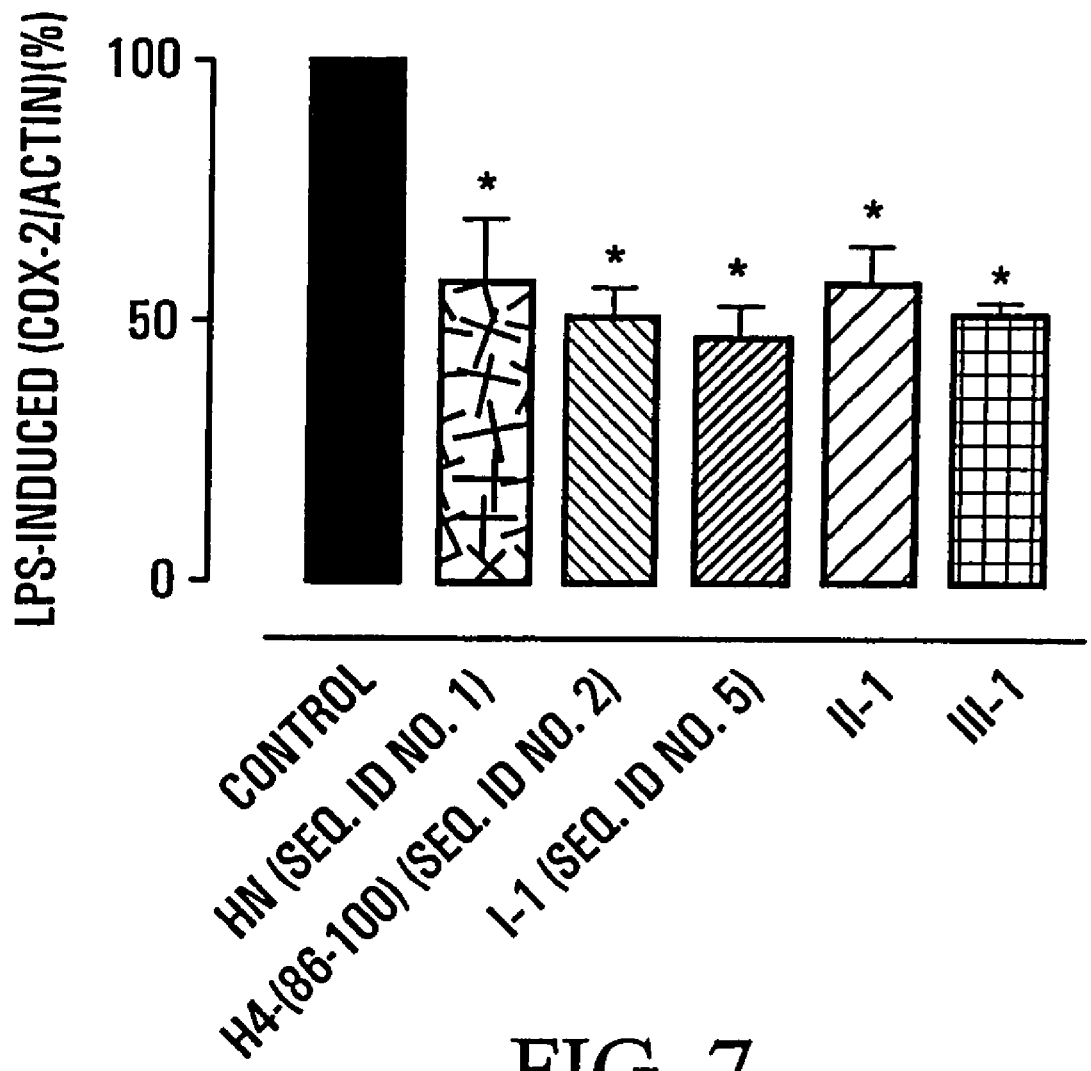
FIG. 7 is a graph showing the inhibitory effects of HN (SEQ ID NO. 1), related peptides and non-peptides on the expression of COX-2 in LPS-stimulated rat alveolar macrophages.

Blockade of morphine tolerance. Morphine, injected twice a day (10 mg/kg, i.p.) for 8 consecutive days in mice, produced an increase in the tail-flick latency that remained significant as compared to the control group (saline) for only 3 days, tolerance being developed at days 6 and 8 (FIG. 5). Compound II-1 (4 mg/kg, twice a day, i.p. in mice) produced a small increase in the tail-flick latency that was significant only on days 1 and 8. Compound II-1 administered 30 min prior to morphine (10 mg/kg) potentiated the analgesic effect of morphine and, on days 6 and 8, inhibited morphine tolerance (FIG. 7; *P<0.05 as compared with control).

Lack of motor effect. All cyclic peptides (compounds I-1 (SEQ ID NO. 5), I-2 (SEQ ID NO. 6), I-3 (SEQ ID NO. 7), I-4 (SEQ ID NO. 8) and I-5 (SEQ ID NO. 9); 10 nmol; i.c.v.) and non-peptides (compounds II-1, II-2, II-3, II-4 and III-1, 10 nmol, i.c.v.) did not cause any motor effect in the mouse rotarod assay.

Example VIII

Inhibition of Cyclooxygenase-2 Induction and Prostaglandin-2 Formation

Animals and Reagents. Lung pathogen-free male Wistar rats weighing 250–275 g were purchased from Harlan-Sprague Dawley (Indianapolis, USA). These animals were shipped behind filter barriers and housed in isolated temperature-controlled quarters in an animal isolator unit (John's Scientific Inc., Toronto, Ont.). Roswell Park Institute medium (RPMI) 1640, Dulbecco's phosphate buffered saline (PBS) and dialysed fetal bovine serum (FBS) were purchased from Wisent Inc. (St-Bruno, Que.). Lipopolysaccharide (LPS, *E. coli*, serotype 0127:B8) was from Sigma Chemical Co. (St-Louis, Mo.).

Isolation of rat Alveolar Macrophages (AM). Animals received a lethal dose of pentobarbital sodium (100 mg/kg, MTC Pharmaceuticals Canada Packers, Cambridge, Ont.), the abdominal aorta was severed, and the trachea was canulated. The lungs were lavaged with six 8-ml aliquots of sterile phosphate-buffered saline (PBS, pH 7.4) with gentle massage of the lungs during the washings as described (Lemaire I. *Am. Rev. Respir. Dis.* 1985, 131, 144–149). Bronchoalveolar (BAL) cells were obtained by centrifugation at 200 g at 4° C. for 5 min, and resuspended in RPMI supplemented with 0.5% dialysed FBS and 0.8% N-2-hydroxyethylpiperazine-N'-2-ethanesulfonic acid (HEPES), which will henceforth be referred to as complete culture medium (CM). Cells were counted in a hemacytometer chamber and viability (99–100%) was determined by trypan blue exclusion. Differential analysis of cytocentrifuge smears of lavage cells (Shandon, $2.5 \times 10^4$ cells) stained with Wright-Giemsa indicated that the BAL cell population is essentially composed of macrophages (99% AM) in normal rats.

Culture and Stimulation of AM. AM ($2 \times 10^5$) were plated into 96-well plates in 200 μl of CM alone or with LPS (1 μg/ml) in the presence and absence of HN (SEQ ID NO. 1) and related compounds at various concentrations as indicated. Cells were incubated for 20 h at 37° C. in 5% $CO_2$. Following incubation, the culture supernatants were collected and frozen at −20° C., and their prostaglandin $E_2$ ($PGE_2$) content was measured within 2 days.

Prostaglandin $E_2$ Determination. Prostaglandin $E_2$ ($PGE_2$) was determined from cell-free supernatants using a competitive enzymeimmunoassay system (Biotrack™, Amersham Pharmacia Biotech). Following dissociation of $PGE_2$ from soluble receptors and interfering binding proteins present in culture media, the assay is based on competition between unlabelled $PGE_2$ and a fixed quantity of peroxidase-labelled $PGE_2$ for a limited number of binding sites on a $PGE_2$ specific antibody. It was performed according to the manufacturer's instruction using two different dilutions of culture media. At least 4 different experiments were performed for each compound and results are expressed as mean±SEM.

COX-1 and COX-2 Immunoblotting. Macrophages were cultured at $10^6$/ml in 24-wells for 20 h in complete medium in the presence or absence of LPS (1 μg/ml). Cells were collected with a rubber policeman, pooled and centrifuged (5 min, 200 ×g). The pellet was washed with PBS (pH 7.4) and frozen at −80° C. The cell pellet from each sample was resuspended in 100 mM Tris, pH 7.4 and sonicated for 15 sec twice with an Ultrasonics™ cell disrupter to lyse the cells. Cell lysates were assayed for protein content by the Bradford method (Bio-Rad Laboratories). Protein from each sample (5 μg–20 μg) was denatured in Laemmli buffer for 5 min and resolved by SDS-gel electrophoresis on a polyacrylamide gel (4% stacking and 10% resolving layer) using an apparatus for minigels (Hoefer Scientific Instruments). After electrophoresis, the proteins were transferred to nitrocellulose membranes with a Transfor™ electrophoresis unit (Hoefer Scientific Instruments). The membranes were blocked overnight at 4° C. in Tris-buffered saline-0.1% Tween™ 20 (TBS-T) supplemented with 3% fat-free dried milk. After rinsing away the blocking solution with TBS-T-1% milk, the membranes were incubated for 90 minutes with primary antibody against COX-2 (1:1000, Cayman) or COX-1 (1:100, Cayman) and against actin (1:250 or 1:2000 for COX-2 and COX-1 detection respectively, Sigma). The specificity of the COX isoform-specific antibodies was tested by Western blotting of purified COX-2 (50ng) and COX-1 (500 ng) electrophoresis standards per lane (Cayman). After washes with TBS-T-1% milk, the membranes were incubated with HRP-conjugated goat anti-rabbit IgG (Santa Cruz) (1:1000 for COX-2 and 1:100 for COX-1) for 1 hr at room temperature. Excess secondary antibody was washed away with TBS-T-1% milk (3×) followed by TBS (5×). The results were visualized after developing with BM chemiluminescence blotting POD substrate (Boehringer) according to the manufacturer's instructions. Scanning densitometry was performed using a Kodak™ digital science Image Station and software. COX-2 and COX-1 signal density was normalized to actin density. Results are expressed as percent of control and represent mean±SEM of at least 3 different experiments.

Figure 6:
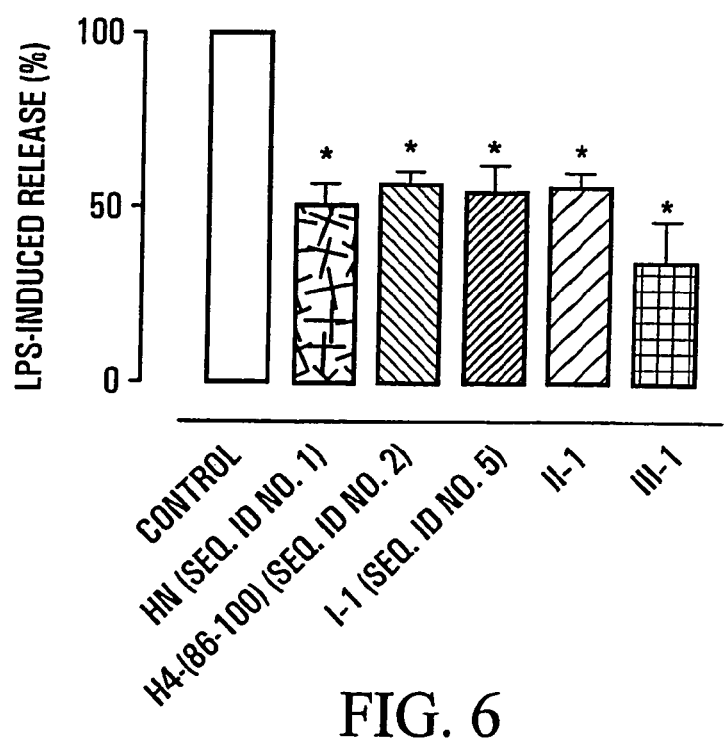
FIG. 6 is a graph showing the inhibitory effects of HN (SEQ ID NO. 1) and related peptides and non-peptides on $PGE_2$ release from LPS-stimulated rat alveolar macrophages.

Results:

Decrease of $PGE_2$ release through inhibition of inducible COX-2 expression. Prostaglandins are known to play an important role in inflammation and transmission of pain. Macrophages stimulated with lipopolysaccharide (LPS, the archetype of bacterial antigen), produce significant amounts of prostaglandins such as $PGE_2$. LPS-stimulated release of $PGE_2$ from isolated rat alveolar macrophages was potently ($10^{-12}$ M–$10^{-7}$ M) and significantly (up to 50%) inhibited by HN (SEQ ID NO. 1) and related compounds. FIG. 6 represents the inhibition observed with $10^{-8}$ M of HN (SEQ ID NO. 1), H4-(86–100) (SEQ ID NO. 2) and compounds of the three Formulae.

Inhibition of LPS-induced COX-2. Cyclooxygenase (COX), the enzymatic system responsible for the formation of $PGE_2$ exists under two isoforms: COX-1 and COX-2. In macrophages, COX-1 is expressed constitutively while COX-2 expression is induced by appropriate stimuli including LPS. The effects of HN (SEQ ID NO. 1) and related compounds were determined on both isoenzymes. HN (SEQ ID NO. 1), H4-(86–100) (SEQ ID NO. 2) and compounds of the three Formulae did not alter the basal level of constitutively expressed COX-1 (not shown) but significantly inhibited LPS induction of COX-2 as assessed by immunoblot analyses (FIG. 7).

Having thus described the invention, it is apparent to one skilled in the art that modifications can be made without departing from the spirit and scope of the claims that now follow.

The invention claimed is:

1. A compound selected from the group consisting of:

N-5-guanidinopentanamide-(2S)-yl-2-N-(p-hydroxyphenylacetyl)phenylenediamine;

N-5-guanidinopentanamide-(2S)-yl-2-N-(p-hydroxyphenylacetyl)-4-trifluoromethyl-phenylenediamine;

N-5-guanidinopentanamide-(2R)-yl-2-N-(p-hydroxyphenylacetyl)-4-carboxy-phenylenediamine;

N-5-guanidinopentanamide-(2R)-yl-2-N-(p-hydroxyphenylacetyl)-4-(p-chlorobenzoyl)-phenylenediamine; and N-5-guanidinopentanamide-(2R)-yl-2-N-(p-hydroxybenzyl)-5-carboxybenzimidazole.

2. A pharmaceutical composition comprising a compound according to claim 1, or a pharmaceutically acceptable salt thereof, in admixture with morphine.

3. A pharmaceutical composition comprising a compound according to claim 1, or a pharmaceutically acceptable salt thereof, in admixture with a pharmaceutically acceptable carrier, diluent or excipient.

4. A method of inhibiting induction of cyclooxygenase-2 (COX-2) in an animal comprising the step of administering to the animal an effective amount of a compound of general formula I or II, or a pharmaceutically acceptable salt thereof:

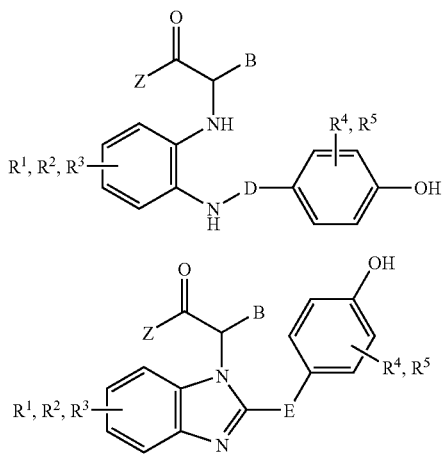

wherein:
B is —$(C_1-C_6)$alkylguanidino, —$(C_1-C_6)$alkyl(4-imidazolyl), —$(C_1-C_6)$alkylamino, p-aminophenylalkyl $(C_1-C_6)$—, p-guanidinophenylalkyl$(C_1-C_6)$— or 4-pyridinylalkyl$(C_1-C_6)$—;
D is —(CO)—, —(CO)—$(C_1-C_6)$alkylene or —$(C_1-C_6)$ alkylene;
E is a single bond or —$(C_1-C_6)$alkylene;
Z is $NH_2$, —NH—$(C_1-C_6)$alkylcarboxyamide, —NH—$(C_1-C_6)$alkyl, —NH—(N-benzyl), —NH-cyclo$(C_5-C_7)$alkyl, —NH-2-(1-piperidyl)ethyl, —NH-2-(1-pyrrolidyl)ethyl, —NH-2-(1-pyridyl)ethyl, —NH-2-(morpholino)ethyl, -morpholino, -piperidyl, —OH, —$(C_1-C_6)$alkoxy, —O-benzyl or —O-halobenzyl;
$R^1$, $R^2$ and $R^3$ are, independent of one another, -hydrogen, arylcarbonylamino, —$(C_1-C_6)$alkoylamino, —$(C_1-C_6)$alkylamino, —$(C_1-C_6)$alkyloxy, —$(C_1-C_6)$ alkylamiocarbonyl, -carboxy, —OH, benzoyl, -p-halogenbenzoyl, -methyl, —S-(2,4-dinitrophenyl), —S-(3-nitro-2-pyridinesulfenyl), -sulfonyl, -trifluoromethyl, —$(C_1-C_6)$alkylaminocarbonylamino, -halo or -amino; and
$R^4$ and $R^5$ are, independent of one another, -hydrogen, —$(C_1-C_6)$alkyl, -methyloxy, -nitro, -amino, -arylcarbonylamino, —$(C_1-C_6)$alkoylamino, —$(C_1-C_6)$alkylamino, -halo or —OH.

5. The method according to claim 4, wherein the compound is administered centrally or peripherally.

6. A method of managing pain in an animal comprising the step of administering to the animal an effective amount of a compound of general formula I or II, or a pharmaceutically acceptable salt thereof:

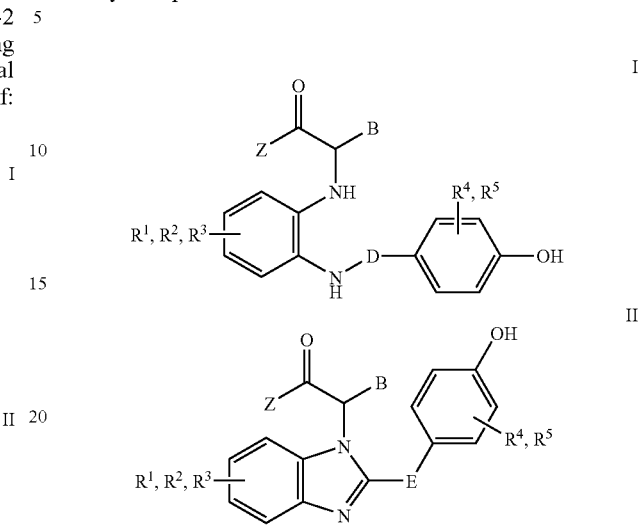

wherein:
B is —$(C_1-C_6)$alkylguanidino, —$(C_1-C_6)$alkyl(4-imidazolyl), —$(C_1-C_6)$alkylamino, p-aminophenylalkyl $(C_1-C_6)$—, p-guanidinophenylalkyl$(C_1-C_6)$— or 4-pyridinylalkyl$(C_1-C_6)$—;
D is —(CO)—, —(CO)—$(C_1-C_6)$alkylene or —$(C_1-C_6)$ alkylene;
E is a single bond or —$(C_1-C_6)$alkylene;
Z is $NH_2$, —NH—$(C_1-C_6)$alkylcarboxyamide, —NH—$(C_1-C_6)$alkyl, —NH—(N-benzyl), —NH-cyclo$(C_5-C_7)$alkyl, —NH-2-(1-piperidyl)ethyl, —NH-2-(1-pyrrolidyl)ethyl, —NH-2-(1-pyridyl)ethyl, —NH-2-(morpholino)ethyl, -morpholino, -piperidyl, —OH, —$(C_1-C_6)$alkoxy, —O-benzyl or —O-halobenzyl;
$R^1$, $R^2$ and $R^3$ are, independent of one another, -hydrogen, arylcarbonylamino, —$(C_1-C_6)$alkoylamino, —$(C_1-C_6)$alkylamino, —$(C_1-C_6)$alkyloxy, —$(C_1-C_6)$ alkylamiocarbonyl, -carboxy, —OH, benzoyl, -p-halogenbenzoyl, -methyl, —S-(2,4-dinitrophenyl), —S-(3-nitro-2-pyridinesulfenyl), -sulfonyl, -trifluoromethyl, —$(C_1-C_6)$alkylaminocarbonylamino, -halo or -amino; and
$R^4$ and $R^5$ are, independent of one another, -hydrogen, —$(C_1-C_6)$alkyl, -methyloxy, -nitro, -amino, -arylcarbonylamino, —$(C_1-C_6)$alkoylamino, —$(C_1-C_6)$alkylamino, -halo or —OH.

7. The method according to claim 6, wherein the compound is administered centrally or peripherally.

8. The method according to claim 7, wherein the compound is administered in conjunction with morphine.

* * * * *